United States Patent [19]
Webb et al.

[11] Patent Number: 5,814,335
[45] Date of Patent: Sep. 29, 1998

[54] SPHINGOSOMES FOR ENHANCED DRUG DELIVERY

[75] Inventors: Murray S. Webb, Vancouver; Marcel B. Bally, Bowen Island; Lawrence D. Mayer, N. Vancouver; James J. Miller, Vancouver; Paul G. Tardi, Richmond, all of Canada

[73] Assignee: Inex Pharmaceuticals Corporation, Canada

[21] Appl. No.: 932,375

[22] Filed: Sep. 17, 1997

Related U.S. Application Data

[63] Continuation of Ser. No. 572,255, Dec. 14, 1995, Pat. No. 5,741,516, which is a continuation-in-part of Ser. No. 481,120, Jun. 7, 1995, abandoned, which is a continuation-in-part of Ser. No. 263,603, Jun. 20, 1994, Pat. No. 5,543,152.

[51] Int. Cl.$^6$ ............................ A61K 9/127; A61K 31/44

[52] U.S. Cl. ............................................... 424/450

[58] Field of Search ................................. 424/450

[56] References Cited

U.S. PATENT DOCUMENTS

| | | |
|---|---|---|
| 4,920,016 | 4/1990 | Allen . |
| 4,981,692 | 1/1991 | Popescu et al. ..................... 424/422 |
| 5,192,549 | 3/1993 | Barenholz et al. . |

OTHER PUBLICATIONS

Hope et al., "Generation of Multilamellar and Unilamellar Phospholipid Vesicles," *Chemistry and Physics of Lipids*, 40:89–107 (1986).

*Primary Examiner*—Nathan M. Nutter
*Attorney, Agent, or Firm*—Townsend and Townsend and Crew LLP

[57] ABSTRACT

Liposomal formulations having extended circulation time in vivo and increased drug retention are comprised of sphingomyelin and cholesterol and have an acidic intraliposomal pH. The formulations have enhanced stability and thus are used in methods which provide improved drug delivery and more effective treatment. The delivery of ciprofloxacin, and alkaloid drugs, particularly swainsonine, vincristine and vinblastine, is significantly improved.

12 Claims, 10 Drawing Sheets

SPHINGOSOMES FOR ENHANCED DRUG DELIVERY

RELATED APPLICATIONS

This is a Continuation of application Ser. No. 08/572,255 filed Dec. 14, 1995, now U.S. Pat. No. 5,741,516, which is a continuation-in-part of application Ser. No. 08/481,120, filed Jun. 7, 1995, and now abandoned, which is a continuation-in-part of application Ser. No. 08/263,603, filed Jun. 20, 1994, and now U.S. Pat. No. 5,543,152, the disclosure of which is incorporated by reference.

BACKGROUND OF THE INVENTION

Liposomal formulations of therapeutically active drugs have significant advantages over drugs injected in free form. Weinstein, *Liposomes: From Biophysics to Therapeutics*, (Ostro, M. J., ed.), Marcel Dekker, Inc., N.Y., pp. 277–338, (1987). For example, liposomal formulations of the anti-cancer alkaloid vincristine have greater efficacy against L1210 leukemia cells than does free vincristine and have reduced collateral toxicity. Mayer et al., *Cancer Chemother. Pharmacol.* 33:17–24 (1993) and Mayer et al., *Cancer Res.* 50:575–579 (1990). The development of liposomal formulations of therapeutic agents with clinical and/or pharmaceutical potential depends on the liposome/drug combination possessing both biological efficacy and long-term chemical stability. In general, the efficacy of a liposomal agent can be improved by increasing both the liposome circulation lifetime and the ability of the liposome to retain the encapsulated drug. Mayer, ibid, and Boman et al., *Cancer Res.* 54: 2830–2833 (1994). Therefore, much effort has focused on the development of liposomal formulations of therapeutic compounds having both extended circulation times and enhanced drug retention.

A wide variety of therapeutic agents can be loaded into liposomes with encapsulation efficiencies approaching 100% by using a transmembrane pH gradient. Mayer et al., *Biochim. Biophys. Acta* 1025:143–151 (1990) and Madden et al., *Chem. Phys. Lipids* 53: 37–46 (1990). The chemical stability of these formulations, i.e., the effective retention of the loaded drugs within the liposomes during circulation in vivo, frequently requires that the intraliposomal pH be in the range between pH 2.0 to 4.0. Within this pH range however, acid hydrolysis of the acyl component of liposomes can destabilize the liposomal membranes and result in premature leakage of the drug.

For example, vincristine can be loaded efficiently into liposomes by a pH gradient-dependent encapsulation procedure which employs an intraliposomal pH of 4.0. Mayer et al., *Biochim. Biophys. Acta* 1025:143–151 (1990) and Mayer et al., *Cancer Res.* 50: 575–579 (1990). The work with liposomal vincristine has been based on vesicles containing phosphatidylcholine (PC), usually egg PC or distearoyl-PC, and cholesterol. Mayer et al., 1993, supra. Increased anti-tumor efficacy of liposomal vincristine occurs when the in vivo retention of vincristine in the liposomes is increased using a 100-fold larger transmembrane pH gradient (i.e. intraliposomal pH=2.0). Boman et al., supra. However, at this pH the acid-hydrolysis of the PC component of the liposomes occurs at a significant rate and severely limits the chemical stability of the liposomes. In particular, the fatty acid carboxyl esters at positions sn-1 and sn-2 are especially susceptible to acid-hydrolysis to produce lyso-PC and free fatty acids. Grit et al., *Chem. Phys. Lipids* 64:3–18 (1993). Liposomes containing significant proportions of lyso-PC are more permeable to solutes, and therefore would be unsuitable as drug delivery vehicles.

It has been reported that sphingomyelin imparts an increase in the circulation lifetime of liposomes. Allen et al., *Biochim. Biophys. Acta* 981:27–35 (1989) and Allen et al., *FEBS Lett.* 223:42–46 (1987). However, these studies employed an entrapped aqueous solute ($^{125}$I-tyraminylinulin) as a marker for liposome distribution, and the apparent increase in liposome longevity in the presence of sphingomyelin may have resulted at least in part from increased solute retention by sphingomyelin. There have also been several reports that sphingomyelin-containing liposomes are more toxic than PC-containing liposomes. Weeeratne et al., *Brit. J. Exp. Pathol.* 64:670–676 (1983), Allen et al., *J. Pharmacol. Exp. Therap.* 229:267–275 (1984), and Allen et al., *Res. Commun. Chem. Pathol. Pharmacol.* 50:281–290 (1985). Although more conclusive studies are not available, the perception is that sphingomyelin-containing liposomes are associated with an increased risk of toxicity.

Liposomal formulations of therapeutic compounds having increased biological and chemical stability are needed in the art. As the efficacy of liposomal agents may be improved by increasing the liposome circulation time and the ability of the liposome to retain the encapsulated drug, the development of liposomal formulations having these properties would be valuable additions to clinical treatment regimens. Quite surprisingly, the present invention fulfills these and other related needs.

SUMMARY OF THE INVENTION

The present invention provides a liposomal composition for delivery of a therapeutic compound to a mammalian host. The composition comprises a liposome having one or more membranes which comprise sphingomyelin and cholesterol, a liposomal interior having a pH less than that of the liposomal exterior, and a therapeutic compound contained in the liposome for delivery to the host. The sphingomyelin and cholesterol are typically present at a molar ratio from 75/25 mol %/mol %, respectively, to 30/50 mol %/mol %, respectively and in a preferred example at a ratio of about 55/45, mol %/mol %, respectively. The lipophilic therapeutic compound may be an alkaloid, such as vincristine, vinblastine, swainsonine, or etoposide or a prodrug thereof. The therapeutic may also be the antibacterial ciprofloxacin or derivative thereof. The drug, such as vincristine, may be present at a drug to lipid ratio of approximately 0.01/1.0 to 0.2/1.0 (wt/wt). Swainsonine may be present at a drug to lipid ratio of 0.01:1.1 to 0.5:1.0 (mol:mol). Targeting ligands and other lipids may also be present as components of the liposome so long as they do not adversely affect the stability of the drug and liposome. The liposomes may be unilamellar or multilamellar, and will typically have mean diameters of about 0.05 microns to 0.45 microns, and more preferably about 0.05 microns to 0.2 microns. The interior of the liposome will typically have at a pH of approximately pH 2 to pH 5, e.g., comprising a citrate buffer at about pH 4.

In other embodiments the invention provides liposomes for delivery of a therapeutic compound which are produced from a mixture which comprises sphingomyelin and cholesterol in a first buffered aqueous solution having an acidic pH greater than pH 2. The liposome is then suspended in a second buffered solution having a pH which is greater than that of the first buffered aqueous solution, thereby forming a transmembrane pH gradient which facilitates the transfer of the therapeutic compound to the liposome. In some embodiments other passive means of drug entrapment at a low intraliposomal pH can also be used in the process. These alternative processes are typically associated with a less efficient drug entrapment of drug and therefore an additional step of separating the liposome from the second buffer containing free drug may be necessary.

The invention also provides methods for enhanced delivery of a lipophilic therapeutic compound such as an alkaloid to a host for treatment. The host in need of the treatment, such as a patient suffering from a tumor, is administered the liposomal composition which comprises a liposome having one or more membranes which comprise sphingomyelin and cholesterol, a liposomal interior having a pH less than that of the liposomal exterior, and a therapeutic compound contained in the liposome for delivery to the host or a pharmaceutically acceptable salt thereof. The pH gradient may be generated by a methylammonium or ethanolammonium concentration gradient. Typically the cholesterol will be present in the liposomal composition at a total molar proportion of 30% to 50%, and more preferably the sphingomyelin and cholesterol are present at a ratio of about 75/25 mol %/mol %, respectively to 30/50 mol %/mol %, respectively. The delivery of an alkaloid compound such as vincristine or swainsonine, or the antibacterial ciprofloxacin, is particularly suitable in these methods. Vincristine and swainsonine may be present at a drug to lipid ratio of approximately 0.01/1.0 to 0.2/1.0 (wt/wt) and 0.01/1.0 to 0.5/1.0 (mol/mol), respectively. In any event, the liposomal composition containing the drug may be administered repeatedly to the host to maintain a concentration of the drug sufficient to inhibit or treat the disease, e.g., a tumor, but less than an amount which causes unacceptable toxicity to the host. Administration may be by a variety of routes, but the alkaloids are preferably given intravenously or parenterally. Swainsonine is conveniently administered orally. The liposomes administered to the host may be unilamellar, having a mean diameter of 0.05 to 0.45 microns, more preferably from 0.05 to 0.2 microns.

The invention also provides methods for delivering to a host an alkaloid immunomodulating compound in a liposomal composition. The host may be suffering from chemotherapy induced immunosuppression and treated, for example, by a liposomal composition of swainsonine. The liposomal composition comprises a liposome having one or more membranes which comprise sphingomyelin and cholesterol, a liposomal interior having a pH less than that of the liposomal exterior, and a therapeutic compound contained in the liposome for delivery to the host or a pharmaceutically acceptable salt thereof. Preferably, swainsonine is given orally, intravenously, or parenterally.

DESCRIPTION OF SPECIFIC EMBODIMENTS

Figure 1:
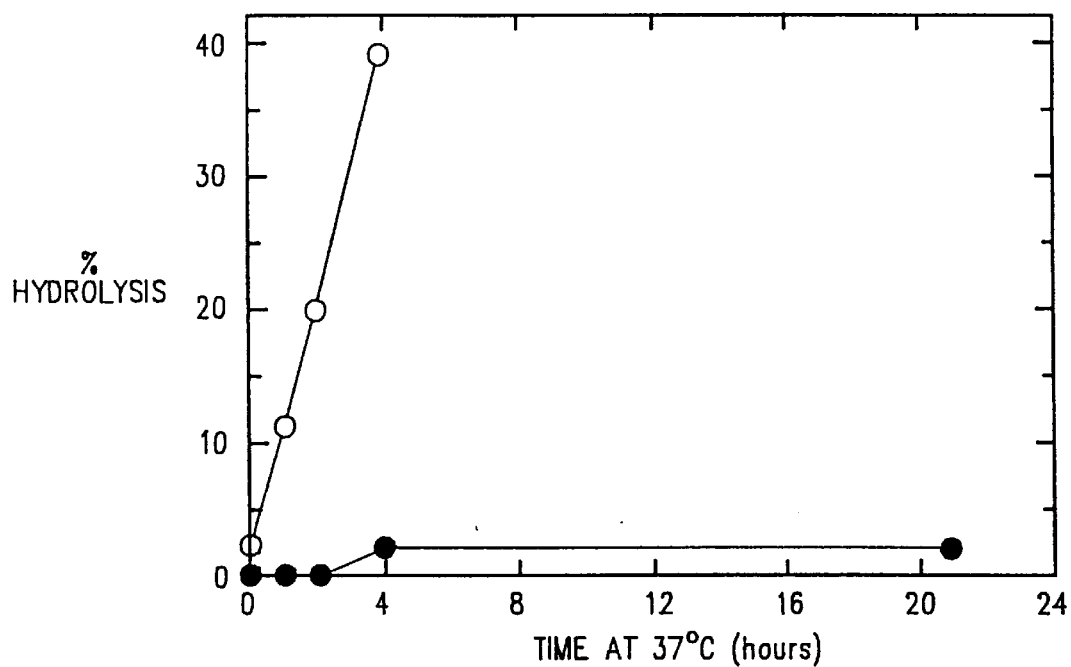
FIG. 1 illustrates the hydrolysis of large unilamellar liposomes of DSPC/Chol (55/45, mol/mol) (○) SM/Chol (55/45, mol/mol) (●) at 37° C. in 0.3M citrate, pH 2.0.

The present invention provides compositions and methods for enhanced delivery of therapeutic compounds to a host. The liposomal formulations of the invention have extended circulation lifetimes and/or enhanced drug retention. The liposomes, also referred to as "sphingosomes," are comprised of sphingomyelin and cholesterol and have an acidic intraliposomal pH. The liposomal formulations based on sphingomyelin and cholesterol have several advantages when compared to other formulations. The sphingomyelin/cholesterol combination produces liposomes which are much more stable to acid hydrolysis, have significantly better drug retention characteristics, have better loading characteristics into tumors and the like, and show significantly better anti-tumor efficacy than other liposomal formulations which were tested.

"Liposome", "vesicle" and "liposome vesicle" will be understood to indicate structures having lipid-containing membranes enclosing an aqueous interior. The structures may have one or more lipid membranes unless otherwise indicated, although generally the liposomes will have only one membrane. Such single-layered liposomes are referred to herein as "unilamellar". Multilayer liposomes are referred to herein as "multilamellar".

The liposome compositions of the present invention are comprised of sphingomyelin and cholesterol. The ratio of sphingomyelin to cholesterol present in the liposome may vary, but generally is in the range of from 75/25 mol %/mol sphingomyelin/cholesterol to 30/50 mol %/mol % sphingomyelin/cholesterol, more preferably about 70/30 mol %/mol sphingomyelin/cholesterol to 40/45 mol %/mol % sphingomyelin/cholesterol, and most preferably is approximately 55/45 mol %/mol % sphingomyelin/cholesterol. Other lipids may be present in the formulations as may be necessary, such as to prevent lipid oxidation or to attach ligands onto the liposome surface. Generally the inclusion of other lipids will result in a decrease in the sphingomyelin/ cholesterol ratio.

A wide variety of therapeutic compounds may be delivered by the liposomes and methods of the present invention. "Therapeutic compound" is meant to include, e.g., nucleic acids, proteins, peptides, oncolytics, anti-infectives, anxiolytics, psychotropics, immunomodulators, ionotropes, toxins such as gelonin and inhibitors of eucaryotic protein synthesis, and the like. Preferred among the therapeutic compounds for entrapment in the liposomes of the present invention are those which are lipophilic cations. Among these are therapeutic agents of the class of lipophilic molecules which are able to partition into the lipid bilayer phase of the liposome, and which therefore are able to associate with the liposomes in a membrane form. Representative drugs include prostaglandins, amphotericin B, methotrexate, cis-platin and derivatives, vincristine, vinblastine, progesterone, testosterone, estradiol, doxorubicin, epirubicin, beclomethasone and esters, vitamin E, cortisone, dexamethasone and esters, betamethasone valerete and other steroids, etc.

Particularly preferred therapeutic compounds for use in the present invention is the fluorinated quinolone antibacterial ciprofloxacin and its derivatives, and the alkaloid compounds and their derivatives. Among the alkaloid derivatives are swainsonine and members of the vinca alkaloids and their semisynthetic derivatives, such as, e.g., vinblastine, vincristine, vindesin, etoposide, etoposide phosphate, and teniposide. Among this group, vinblastine and vincristine, and swainsonine are particularly preferred. Swainsonine (Creaven and Mihich, *Semin. Oncol.* 4:147 (1977) has the capacity to stimulate bone marrow proliferation (White and Olden, *Cancer Commun.* 3:83 (1991)). Swainsonine also stimulates the production of multiple cytokines including IL-1, IL-2, TNF, GM-CSF and interferons (Newton, *Cancer Commun.* 1:373 (1989); Olden, K., *J. Natl. Cancer Inst.,* 83:1149 (1991)). It also reportedly induces B- and T-cell immunity, natural killer T-cell and macrophage-induced destruction of tumor cells in vitro and, when combined with interferon, has direct anti-tumor activity against colon cancer and melanoma cancers in vivo (Dennis, J., *Cancer Res.,* 50:1867 (1990); Olden, K., *Pharm. Ther.* 44:85 (1989); White and Olden, *Anticancer Res.,* 10:1515 (1990)). Other alkaloids useful in the present invention include paclitaxel (taxol) and synthetic derivatives thereof.

A representative method for producing the liposomes of the invention is now described, although it will be understood that the procedure can be subjected to modifications in various aspects without affecting the outcome. As described more fully below in the experimental section, liposomes are prepared which are able to entrap lipophilic cationic drugs in response to transmembrane pH gradients, yet which liposomes are resistant to drug leakage in the circulation. Initially, liposomes containing sphingomyelin and cholesterol are prepared according to the desired molar ratio of sphingomyelin and cholesterol, e.g., 55/45 mol./mol., respectively. An appropriate buffer for formation of the liposome, and thus for forming the liposomal interior, is one which is physiologically acceptable and having an acid pH, typically about pH 2 to about pH 6, more preferably about pH 3 to pH 5, and most preferably at about pH 4. An example of an appropriate entrapment buffer is citrate buffer, adjusted to approximately pH 4.

Other lipids can also be included in the preparation of the liposome. These lipids include phospholipids such as phosphatidylcholine, phosphatidylethanolamine, and phosphatidylserine, phosphatidylglycerol, phosphatidic acid, cardiolipin, and phosphatidylinositol, with varying fatty acyl compositions and of natural and/or (semi)synthetic origin, and dicetyl phosphate. Ceramide and various glycolipids, such as cerebrosides or gangliosides, may also be added. Cationic lipids may also be added. Additional lipids which may be suitable for use in the liposomes of the present invention are well known to persons skilled in the art.

Once the liposomes are prepared with the entrapped acidic buffer the liposomes can be sized to a desired size range. The liposomes should generally be less than about 1.0 microns in size, preferably approximately 0.05 to 0.45 microns, more preferably about 0.05 to 0.2 microns, which allows the liposome suspension to be sterilized by filtration. For sizing liposomes, a liposome suspension may be sonicated either by bath or probe down to small vesicles of less than about 0.05 microns in size. Homogenization may also be used to fragment large liposomes into smaller ones. In both methods the particle size distribution can be monitored by conventional laser-beam particle size discrimination or the like.

Extrusion of liposomes through a small-pore polycarbonate membrane or an asymmetric ceramic membrane is an effective method for reducing liposome sizes to a relatively well defined size distribution. Typically the suspension is cycled through the membrane one or more times until the desired liposome size distribution is achieved. The liposomes can be extruded through successively smaller pore membranes to achieve a gradual reduction in liposome size.

Before or after sizing, the external pH of the liposome preparation is increased to about pH 7.0 to 7.5, by the addition of suitable buffer, e.g., 0.5M $Na_2HPO_4$. The drug or drugs of choice are then admixed with the liposomes at an appropriate concentration, e.g., a vincristine/lipid ratio of 0.01/1.0 to 0.2/1.0 (wt/wt), for a time and under conditions sufficient to allow transmembrane uptake of the drug(s), e.g., from about 5 to 30 min. or more and at about 45°–65° C. (e.g., 10 min. at 60° C. in the case of the liposomal vincristine preparations described in the Examples below), although one of ordinary skill in the art will understand that the conditions may be adjusted and uptake monitored accordingly. The formulation of liposomes and therapeutic compound(s) should generally consist of a relatively uniform population of vesicles in terms of size and drug-lipid ratio.

Procedures for passive entrapment of drugs other than the direct formation of pH transmembrane gradients can be used. In one embodiment internal/external concentration gradients are formed employing the charged amines: methylammonium or ethanolammonium. Liposomes are formed in the presence of an aqueous solution of the charged amine. Any number of pharmaceutically acceptable salts of the charged amine may be used to prepare the solution such as, but not limited to, fluoride, chloride, citrate, sulfate, phosphate, bromide, iodide, or acetate. After formation of the liposome, external charged amines are diluted or removed by, for example, dilution, filtration, dialysis or gel exclusion. A internal/external pH gradient is thereby generated as uncharged amines leave the liposomal interior and leave behind a proton. The size of the pH gradient will be proportional to the size of the concentration gradient formed. The pH gradient is employed to load the liposome with a drug, such as swainsonine or ciprofloxacin, per methods disclosed herein and as described in U.S. Pat. No. 5,192,549 or copending U.S. application Ser. No. 08/399, 692, filed Feb. 27, 1995. Briefly, following preparation of the concentration gradient across the liposome membrane, the resulting liposome is incubated with a neutral form of the protonatable therapeutic agent which is drawn into the liposome as a result of the concentration gradient and, once encapsulated, protonated and trapped. Subsequent loading of the protonatable therapeutic agent into the liposomes will be dependent on the methylamine concentration gradient (or methylammonium ion gradient) and the pH gradient which also results from a change in methylamine concentration between the lipid bilayers. The gradients are created by forming liposomes in a methylammonium salt solution, followed by removal or dilution of the salt from the external aqueous phase of the liposomes. The concentration of the methylammonium salt solution which is encapsulated can vary from about 50 mM to about 1M, however concentrations of 200 mM to 800 mM are preferred, with 300 mM to 600 mM being particularly preferred. In general an initial methylammonium ion concentration of about 600 mM is the most preferred. To create the concentration gradient, the original external medium is replaced by a new external medium having a lesser concentration of methylammonium. The replacement of the external medium can be accomplished by various techniques, such as, by passing the lipid vesicle preparation through a gel filtration column, e.g., a Sephadex column, which has been equilibrated with the new medium, or by centrifugation, dialysis, or related techniques. Preferably, ciprofloxacin is loaded via a methylamine or amine concentration gradient. Generally, the ciprofloxacin to lipid ratio will range from about 0.05:1 (mol:mol) to about 1:1 (mol:mol), preferably about 0.3:1 (mol:mol) to 0.5:1 (mol:mol).

Additional components may be added to the liposomes to target them to specific cell types. For example, the liposomes can be conjugated to monoclonal antibodies or binding fragments thereof that bind to epitopes present only on specific cell types, such as cancer-related antigens, providing a means for targeting the liposomes following systemic administration. Alternatively, ligands that bind surface receptors of the target cell types may also be bound to the liposomes. Other means for targeting liposomes may also be employed in the present invention.

Following a separation step as may be necessary to remove free drug from the medium containing the liposome, the liposome suspension is brought to a desired concentration in a pharmaceutically acceptable carrier for administration to the patient or host cells. Many pharmaceutically acceptable carriers may be employed in the compositions and methods of the present invention. A variety of aqueous carriers may be used, e.g., water, buffered water, 0.4% saline, 0.3% glycine, and the like, and may include glycoproteins for enhanced stability, such as albumin, lipoprotein, globulin, etc. Generally, normal buffered saline (135–150 mM NaCl) will be employed as the pharmaceutically acceptable carrier, but other suitable carriers will suffice. These compositions may be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. These compositions may be sterilized techniques referred to above or produced under sterile conditions. The resulting aqueous solutions may be packaged for use or filtered under aseptic conditions and lyophilized, the lyophilized preparation being combined with a sterile aqueous solution prior to administration.

The concentration of liposomes in the carrier may vary. Generally, the concentration will be about 20–200 mg/ml, usually about 50–150 mg/ml, and most usually about 75–125 mg/ml, e.g., about 100 mg/ml. Persons of skill may vary these concentrations to optimize treatment with different liposome components or for particular patients. For example, the concentration may be increased to lower the fluid load associated with treatment.

The present invention also provides methods for introducing therapeutic compounds into cells of a host. The methods generally comprise administering to the host a liposome containing the therapeutic compound, wherein the liposome has a membrane comprised of sphingomyelin and cholesterol and, optionally, other lipids, and an aqueous interior at a pH substantially below physiologic pH, e.g., pH 3 to about 5, and the therapeutic compound of interest. The host may be a variety of animals, including humans, non-human primates, avian species, equine species, bovine species, swine, lagomorpha, rodents, and the like.

The cells of the host are usually exposed to the liposomal preparations of the invention by in vivo administration of the formulations, but ex vivo exposure of the cells to the liposomes is also feasible. In vivo exposure is obtained by administration of the liposomes to host. The liposomes may be administered in many ways. These include parenteral routes of administration, such as intravenous, intramuscular, subcutaneous, and intraarterial. Generally, the liposomes will be administered intravenously or in some cases via inhalation. Often, the liposomes will be administered into a large central vein, such as the superior vena cava or inferior vena cava, to allow highly concentrated solutions to be administered into large volume and flow vessels. The liposomes may be administered intraarterially following vascular procedures to deliver a high concentration directly to an affected vessel. In some instances, the liposomes may be administered orally or transdermally, although the advantages of the present invention are best realized by parenteral administration. For example, swainsonine is conveniently administered orally, but may be administered parenterally or intravenously. The antibacterial ciprofloxacin, described in U.S. Pat. No. 4,670,444, is administered intratracheally, as well as topically, intravenously or parenterally. Intratracheal administration may be provided as a liquid, preferably as an aerosol. For example, nebulizers may be used to create aerosols of droplets of between 70–100 µm in diameter. It will be understood that droplet size should generally be of greater size than the liposomes. Liposomal formulations for topical administration may be incorporated into any of a number of formulations such hydroxypropylmethyl cellulose gels and pastes. For example, hydroxypropylmethyl celluose of 1–4% provides a stable excipient for topical administration. The liposomes may also be incorporated into implantable devices for long duration release following placement. For example, silicone catheters may be coated with ciprofloxacin by incubation with liposomal vesicles of SM/Cholesterol/N,N-dioleyoy-N,N-dimethylammonium chloride (50 mole/40 mole/10 mole) in a solution of 0.3M sucrose.

As described above, the liposomes will generally be administered parenterally, intravenously or via inhalation in the methods of the present invention. Often multiple treatments will be given to the patient. The dosage schedule of the treatments will be determined by the disease and the patient's condition. Standard treatments with therapeutic compounds that are well known in the art may serve as a guide to treatment with liposomes containing the therapeutic compounds. The duration and schedule of treatments may be varied by methods well known to those of skill, but the increased circulation time and decreased in liposome leakage will generally allow the dosages to be adjusted downward from those previously employed. The dose of liposomes of the present invention may vary depending on the clinical condition and size of the animal or patient receiving treatment. The standard dose of the therapeutic compound when not encapsulated may serve as a guide to the dose of the liposome-encapsulated compound. The dose will typically be constant over the course of treatment, although in some cases the dose may vary. Standard physiological parameters may be assessed during treatment that may be used to alter the dose of the liposomes of the invention.

The following examples are offered by way of illustration and not limitation.

EXAMPLE I

Acid Stability of DSPC/Chol vs. SM/Chol Liposomes

This Example demonstrates the stability of liposomes prepared with sphingomyelin and cholesterol to acid hydrolysis compared to liposomes prepared with distearoylphosphatidylcholine and cholesterol.

For liposome preparation, distearoylphosphatidylcholine (DSPC) and egg sphingomyelin (SM) were obtained from Avanti Polar Lipids and used without further purification. Cholesterol was obtained from Sigma Chemical Company, and PEG-PE was synthesized according to Parr et al., submitted, *Biochim. Biophys. Acta* (1994). Lipids were dissolved in $CHCl_3$, or $CHCl_3$ with trace amounts of $CH_3OH$, then mixed at molar ratios as indicated below and excess solvent removed under a stream of nitrogen gas. Residual solvent was removed from the lipid film under high vacuum for 3 to 16 hrs. Lipids were dispersed by the addition of 0.3M citrate buffer (pH 4.0 or 2.0) to achieve a final lipid concentration of either 50 or 100 mg/ml. Hydration of the lipid was facilitated by vortexing and heating to 65° C. Equilibration of the solute between the inside and outside of the liposomes was achieved by five freeze/thaw cycles between −196° and 60° C. as described generally in Mayer et al., *Biochim. Biophys. Acta* 817:193–196 (1985), incorporated herein by reference. Large unilamellar vesicles were produced by repeated extrusion of the multilamellar liposomes through two or three stacked 0.1 µm filters (Poretics, Livermore Calif.) held at 60°–65° C. in a Themobarrel Extruder (Lipex Biomembranes, Vancouver, Canada). Liposome size distributions were confirmed by quasi-elastic light scattering using a Nicomp Model 270 Submicron Particle Sizer; these preparations typically had mean diameters of 130 to 150 nm.

Large unilamellar liposomes of DSPC/Chol or SM/Chol were prepared as described above in 0.3M citrate buffer at pH 2.0 and were then diluted to 3.2 mg/ml of lipid. The liposomes were incubated at 37° C. for various times then frozen prior to the determination of lipid hydrolysis. Lipid dispersions were thawed then the lipid extracted into $CHCl_3/CH_3OH$ and concentrated under a stream of nitrogen gas. Known quantities of lipid were spotted onto K6F thin layer chromatography plates and developed in $CHCl_3/CH_3/OH/H_2O/NH_4OH$ (65/25/4/0.3, by volume). Lipids were visualized in iodine vapor then the appropriate regions of the plate were recovered and analyzed for phosphorous according to Bartlett, *J. Biol. Chem.* 234:466–468 (1959), incorporated herein by reference. Total hydrolysis of DSPC was determined from the amount of MSPC present in the samples and then corrected to total hydrolysis; hydrolysis of sphingomyelin was calculated from the difference between the amount of lipid chromatographed and that recovered as non-hydrolyzed sphingomyelin. Calibration curves were determined for each of DSPC, MSPC and sphingomyelin.

As shown in FIG. 1, liposomes composed of SM/Chol (55/45, mol/mol) were significantly less susceptible to acid hydrolysis than were liposomes composed of DSPC/Chol (55/45, mol/mol). That is, the rate of hydrolysis at 37° C. and pH 2.0 was approximately 100-fold slower in SM/Chol liposomes than in DSPC/Chol liposomes. Similar results were observed during incubation of liposomes at pH 4.0 and at various temperatures between 4° C. and 37° C.

These results indicate that liposomes composed of SM/Chol were significantly more stable to acid hydrolysis than were identical liposomes composed of DSPC/Chol (FIG. 1). As the primary degradation product in DSPC/Chol liposomes is the lyso-PC (MSPC), it is very likely that SM/Chol liposomes are more stable than any formulations based on lipids containing carboxyl-esterified fatty acids (i.e. any phospholipid-based formulations).

EXAMPLE II

Lipid and Drug Pharmacokinetics

Uptake of vincristine into large unilamellar liposomes was achieved using a pH gradient-dependent procedure described by Mayer et al., *Cancer Chemother. Pharmacol.* 33:17–24 (1993), incorporated herein by reference. Briefly, a solution of vincristine sulfate (Oncovin®, Eli Lilly, Indianapolis, Ind.) was added to liposomes at a drug/lipid ratio of 0.1/1 (wt/wt) and equilibrated at 60° C. for 5 to 10 minutes. Vincristine uptake in response to a transmembrane pH gradient was initiated by the addition of 0.5M $Na_2HPO_4$ to bring the external pH to 7.2–7.6. Uptake was allowed to proceed for 10 minutes at 60° C. and typically had a trapping efficiency of approximately 95% (Mayer et al., *Cancer Chemother. Pharmacol.* 33:17–24 (1993)).

Liposomes of DSPC/Chol (55/45), SM/Chol (55/45) or SM/Chol/PEG-PE (55/40/5) containing the non-exchangeable and non-metabolized radiolabel $^{14}$C-CHDE (cholesteryl-4-hexadecyl ether radiolabeled with $^3$H or $^{14}$C, as indicated, obtained from New England Nuclear) were prepared. Empty liposomes or liposomes loaded with $^3$H-vincristine (Amersham) were diluted to the indicated concentration with HBS then injected intravenously into BDF1 mice (8–10 weeks old; Charles River) at a vincristine dose of 2 mg/kg (lipid dose of 20 mg/kg). At various times following the liposome injection, blood was obtained by heart puncture and liver, spleen and muscle recovered. In all cases, lipid and vincristine distributions were determined by liquid scintillation counting of known volumes of plasma and 10% homogenates of the tissues.

Figure 2A:
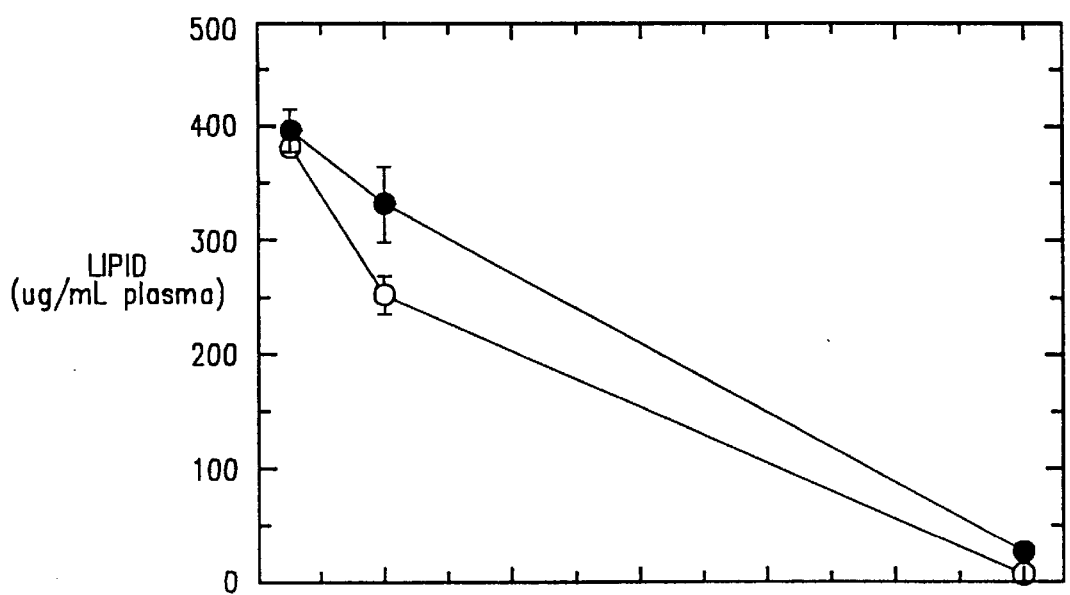
FIG. 2A and FIG. 2B illustrate the amount of lipid remaining in circulation in BDF1 mice injected with large unilamellar liposomes of DSPC/Chol (55/45, mol/mol) (○), SM/Chol (55/45, mol/mol) (●) or SM/Chol/PEG-PE (55/40/5, mol/mol/mol) (■). Injected liposomes were either empty (FIG. 2A) or loaded with vincristine at a drug/lipid ratio of approximately 0.1 (FIG. 2B). The injected dose of lipid was 20 mg/kg, corresponding to a total injection of approximately 430 μg of lipid.
Figure 2B:
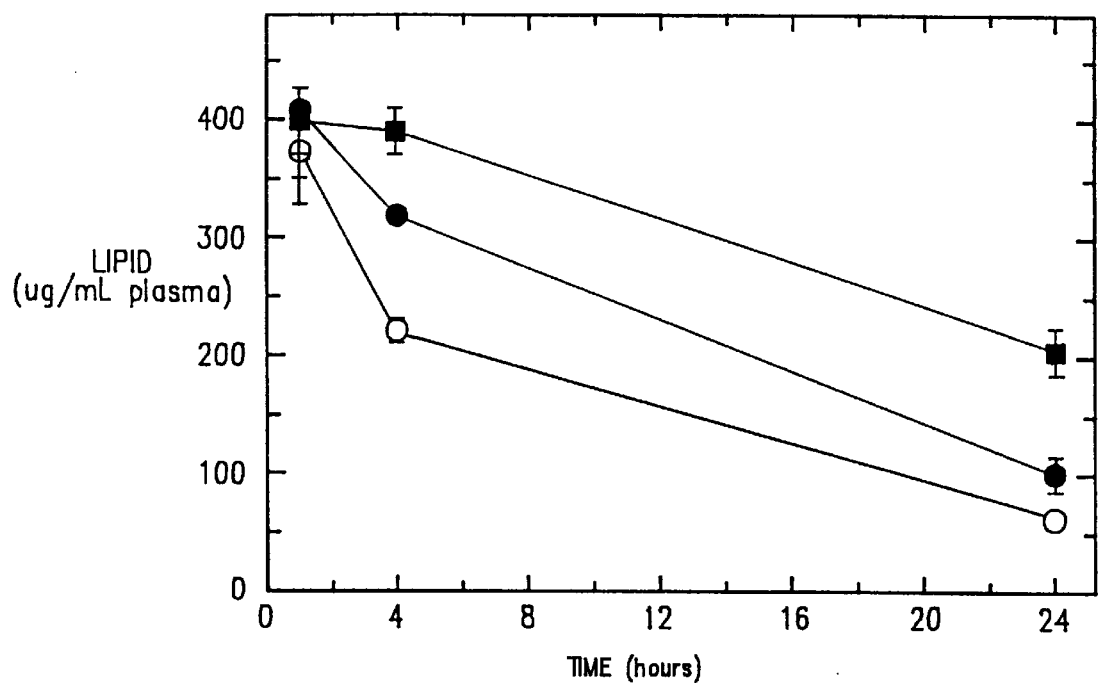

The clearance of empty liposomes of DSPC/Chol and SM/Chol is shown in FIG. 2A. Liposomes composed of SM/Chol were removed from circulation at a slightly slower rate than were DSPC/Chol liposomes. This difference in clearance rates between DSPC/Chol liposomes and SM/Chol liposomes was also observed in formulations containing vincristine, as shown in FIG. 2B, although the overall clearance rates were slower in the presence of vincristine due to the effect of the drug on RES activity. The amount of SM/Chol remaining in circulation was typically 30–50% higher than for DSPC/Chol liposomes. A further increase in the amount of lipid in circulation was achieved by the addition of 5 mol % PEG-PE to the SM/Chol mixtures; 24 hours after i.v. injection, 200 µg lipid/ml plasma remained in circulation for SM/Chol/PEG-PE liposomes compared with 100 µg/ml plasma for SM/Chol liposomes and 65 µg/ml plasma for DSPC/Chol liposomes (FIG. 2B).

Figure 3:
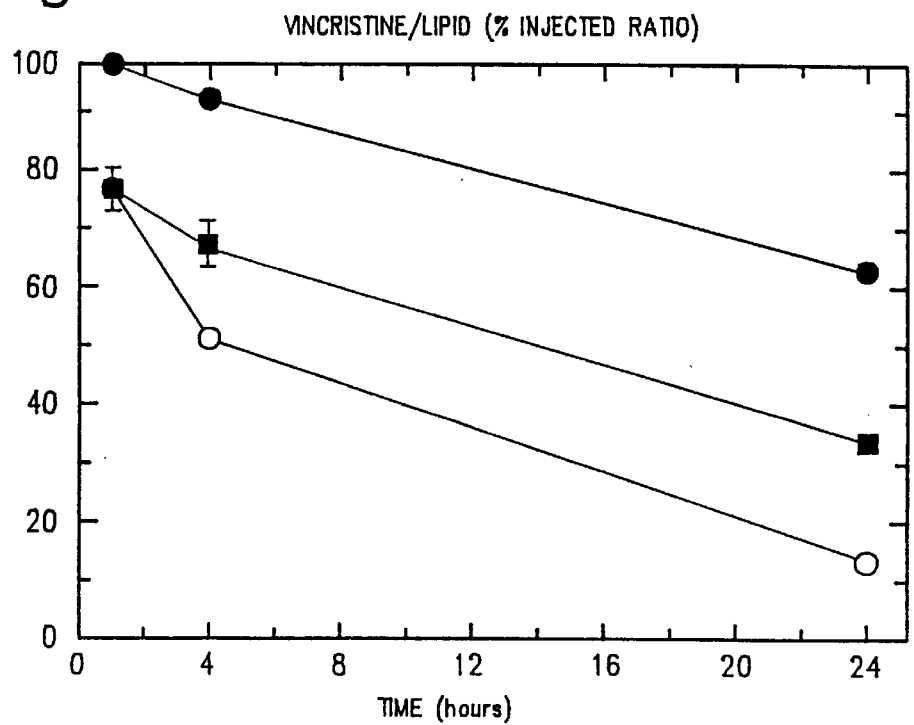
FIG. 3 depicts the vincristine/lipid ratio in the plasma of BDF1 mice at various times after the injection of large unilamellar liposomes of DSPC/Chol (55/45, mol/mol) (○), SM/Chol (55/45, mol/mol) (●) or SM/Chol/PEG-PE (55/40/5, mol/mol/mol) (■). Mice were injected with liposomes at a vincristine/lipid ratio of approximately 0.1, corresponding to a lipid dose of 20 mg/kg and a vincristine dose of 2.0 mg/kg. Total amounts injected were approximately 430 μg of lipid and 43 μg of vincristine.

The drug retention characteristics of the liposomes were significantly altered by changes in the lipid composition of the vesicles. Vincristine leakage from DSPC/Chol liposomes was very rapid, with only 50% of the originally encapsulated vincristine remaining entrapped after 4 hours in circulation, as shown in FIG. 3. In contrast, vincristine leakage from SM/Chol liposomes was much slower, with greater than 60% of the entrapped drug remaining in the liposomes 24 hours after injection (FIG. 3). Furthermore, additional increases in the retention of vincristine in SM/Chol liposomes were not observed in the presence of a two-fold greater transmembrane pH gradient (i.e., $pH_i$=2.0). The presence of 5 mol % PEG-PE in SM/Chol liposomes caused a significant increase in the permeability of vincristine; approximately 30% of the entrapped vincristine remained in the liposomes after 24 hours in circulation, as shown in FIG. 3.

Figure 4:
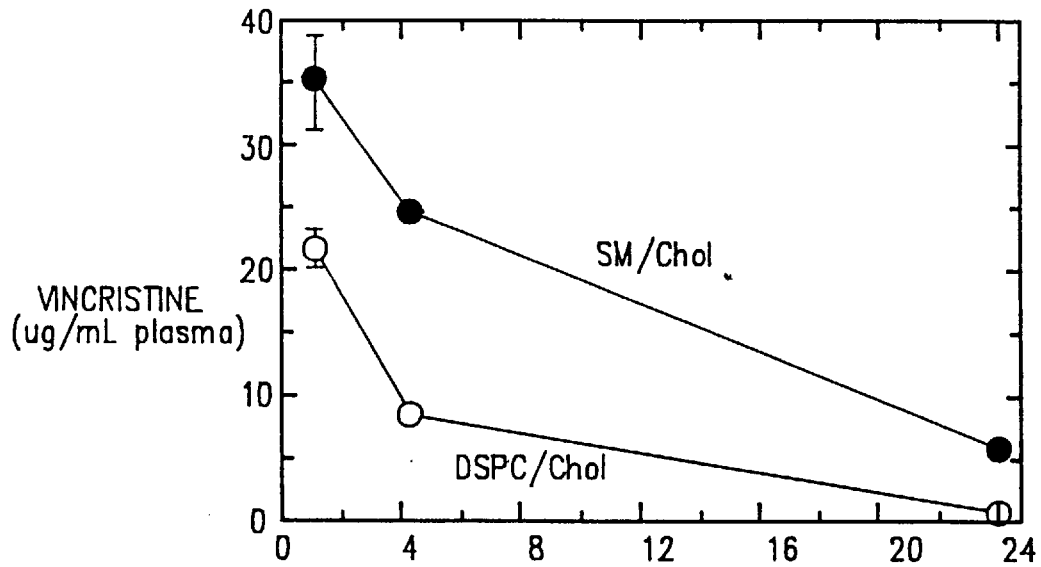
FIG. 4 shows the total vincristine remaining in the plasma of BDF1 mice at various times after the injection of large unilamellar liposomes of DSPC/Chol (55/45, mol/mol) (○), SM/Chol (55/45, mol/mol) (●) or SM/Chol/PEG-PE (55/40/5, mol/mol/mol) (■). Mice were injected with liposomes at a vincristine/lipid ratio of approximately 0.1, corresponding to a lipid dose of 20 mg/kg and a vincristine dose of 2.0 mg/kg. Total amounts injected were approximately 430 μg of lipid and 43 μg of vincristine.

Anti-tumor efficacy of liposomal vincristine is a function of the amount of the drug remaining in circulation and, therefore, is a consequence of both liposome longevity in circulation and drug retention within the liposomes. The total amount of vincristine remaining in circulation was significantly lower in the liposomal DSPC/Chol formulations than in either the liposomal SM/Chol or SM/Chol/PEG-PE formulations, as shown in FIG. 4. Both sphingomyelin-based liposome formulations had identical amounts of vincristine remaining in circulation. This was a consequence of the higher vincristine/lipid ratio in SM/Chol than in SM/Chol/PEG-PE (FIG. 3) and the lower amount of lipid remaining in circulation in SM/Chol than in SM/Chol/PEG-PE (FIG. 2B).

To determine whether the extended circulation lifetime of SM/Chol liposomes was a consequence of reduced uptake of the SM/Chol liposomes by macrophages, the uptake of liposomes by peritoneal macrophages was measured. Empty DSPC/Chol and SM/Chol liposomes containing $^{14}$C-CHDE were prepared as described above and the external pH brought to 7.2 to 7.6 with 0.5M $Na_2HPO_4$. Liposomes were injected i.p. into CD1 mice (8–10 weeks old) (Charles River) at 100 mg lipid/kg in a volume of 0.5 ml. After 4 hrs, peritoneal macrophages were recovered by lavage, purified by repeated centrifugation and then macrophages counted with a hemocytometer and the amount of lipid taken up by the macrophages was determined by liquid scintillation counting.

For serum protein binding assays, 10 mg of either DSPC/Chol or SM/Chol liposomes labelled with $^{14}$C-CHDE were brought to external pH of 7.2–7.6, then diluted to 20 mg/ml with HBS. Liposomes were incubated with 500 µl of fetal bovine serum (ICN Biomedicals) (pre-filtered through a 0.22 µm filter) for 30 mins at 37° C. Serum protein that was not bound to the liposomes was removed by passing the sample over a 1 cm (internal diameter)×18 cm BioGel A-15m column (Bio-Rad Laboratories) (in HBS) at 35 ml/hr. Fractions (1 ml) were assayed for protein (Sigma bicinchoninic acid protein assay kit) and lipid (LSC) and the adsorbed protein was calculated after correction for co-eluting serum protein.

Figure 5:
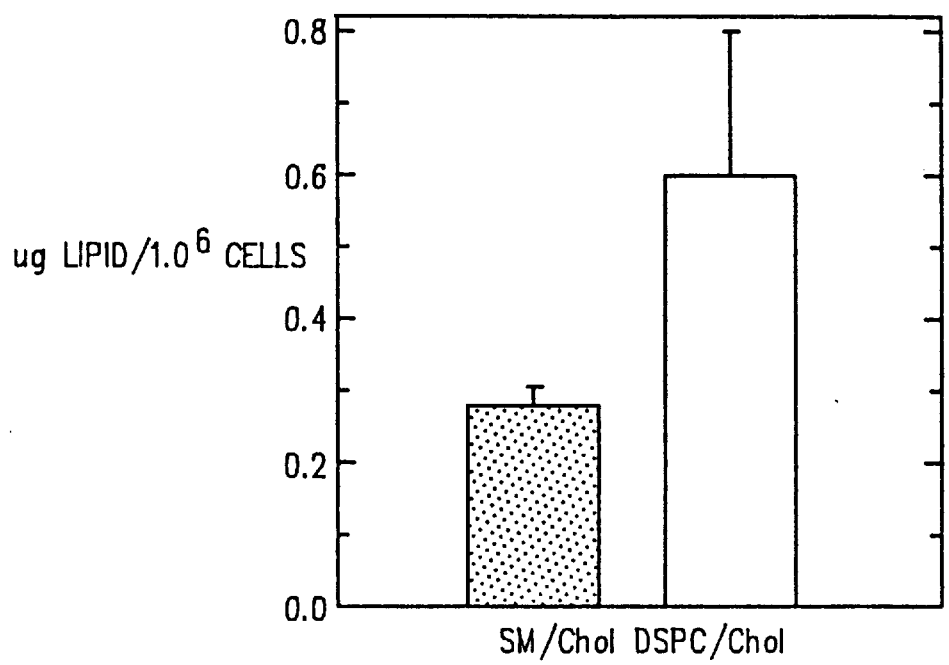
FIG. 5 shows the uptake of large unilamellar liposomes of SM/Chol (55/45, mol/mol) and DSPC/Chol (55/45, mol/mol) by peritoneal macrophages. Liposomes containing the non-exchangeable and non-metabolized radiolabel $^{14}$C-CHDE were injected parenterally at 100 mg/kg. After 4 hrs, macrophages were recovered by lavage and cells and lipid determined by hemocytometry and liquid scintillation counting, respectively.

The uptake of i.p.-injected SM/Chol liposomes into macrophages was 50% lower than the uptake of DSPC/Chol liposomes, as shown in FIG. 5. It is likely that the reduced uptake of SM/Chol liposomes by macrophages and their extended circulation longevity was a consequence of lowered protein opsonization to the surface of SM/Chol liposomes than to DSPC/Chol liposomes. Measurement of the adsorption of fetal bovine serum proteins to SM/Chol and DSPC/Chol liposomes indicated that the DSPC/Chol liposomes adsorbed 13.7 µg protein/mg lipid. In contrast, significant adsorption of fetal bovine serum proteins to SM/Chol liposomes was not detected.

Thus, from this Example it can be seen that liposomes composed of SM/Chol had circulation lifetimes slightly longer than similar DSPC/Chol liposomes, both in the presence and absence of entrapped vincristine (FIG. 2). SM/Chol liposomes were dramatically better than DSPC/Chol liposomes at retaining vincristine that had been encapsulated using the transmembrane pH gradient method (FIG. 4). The addition of PEG-PE to SM/Chol liposomes significantly increased the circulation longevity of the liposomes, but PEG-PE also caused a significant increase in the leakage of vincristine from the liposomes. The increased levels of vincristine remaining in circulation in SM/Chol and SM/Chol/PEG-PE liposomal formulations (FIG. 4) was a consequence of both improved drug retention in SM-containing liposomes (FIG. 3) and the increased circulation longevity of SM/Chol/PEG-PE liposomes (FIG. 2b). However, the increased circulation lifetimes of SM/Chol/PEG-PE liposomes were balanced by the lower drug retention by liposomes containing PEG-PE. Therefore, in SM-based liposomal formulations of vincristine, there was no improvement in vincristine circulation longevity by the addition of the lipid PEG-DSPE (FIG. 4). Furthermore, since there was no improvement in vincristine retention in vivo by the use of a $pH_i=2.0$, the optimal vincristine retention in circulation was achieved with a relatively simple liposomal formulation comprised of only sphingomyelin, cholesterol and citrate buffer (pH 4.0).

EXAMPLE III

Tumor Loading Of Liposomal Vincristine

To determine whether increased vincristine longevity in circulation, as shown in FIG. 4, resulted in increased drug delivery to tumors, the loading of liposomal vincristine into P388 tumors was examined. For tumor loading experiments, BDF1 mice were injected i.p. with $10^6$ P388 cells (obtained from National Cancer Institute, Bethesda, Md.) (passaged weekly in BDF1 mice) 24 hrs prior to the liposome injection. At various times following the liposome injection the tumor was recovered by peritoneal lavage. In all cases, lipid and vincristine distributions were determined by liquid scintillation counting of known volumes of lavage.

Figure 6:
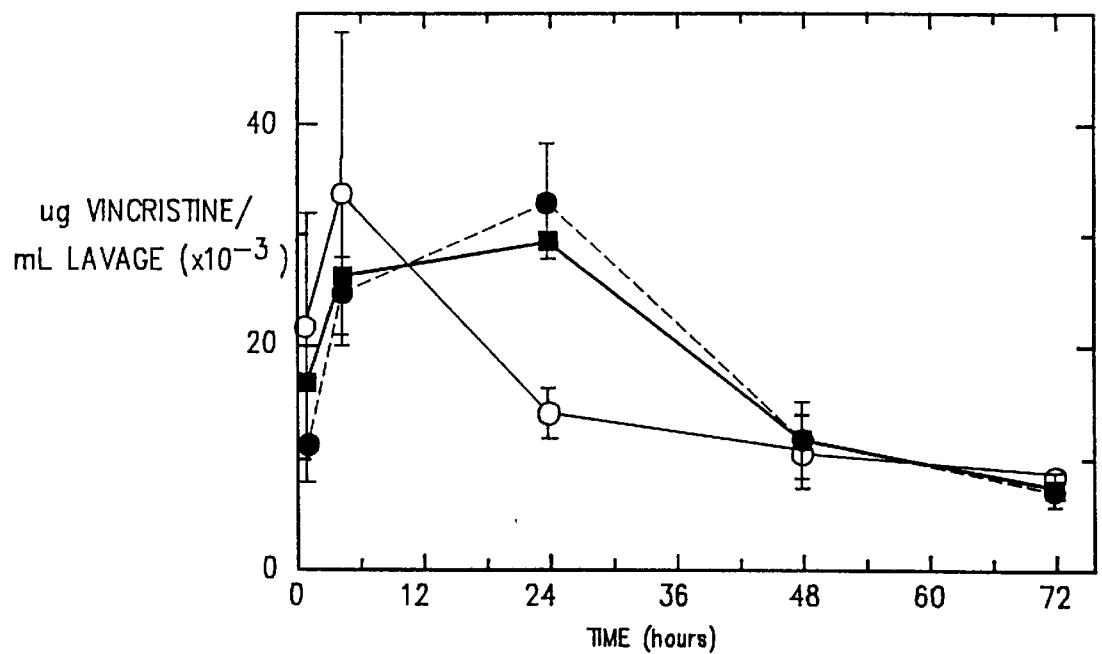
FIG. 6 depicts the loading of vincristine in P388 tumors. Delivery of vincristine to peritoneal P388 tumors in BDF1 mice after i.v. injection of large unilamellar liposomes of DSPC/Chol (55/45. mol/mol) (○), SM/Chol (55/45, mol/mol) (●) or SM/Chol/PEG-PE (55/40/5, mol/mol/mol) (■) containing vincristine at a drug/lipid ratio of 0.1 (wt/wt). Vincristine was injected at a dose of 20 mg/kg, representing a lipid dose of 20 mg/kg.

As shown in FIG. 6, accumulation of vincristine from DSPC/Chol liposomes in P388 tumors had an early peak at 4 hours after liposome injection and was significantly lower at later times. In contrast, vincristine from formulations of both SM/Chol and SM/Chol/PEG-PE showed sustained delivery of vincristine for up to 24 to 48 hours after liposome injection. That is, SM/Chol and SM/Chol/PEG-PE formulations of vincristine delivered at least 30% more vincristine to P388 tumors than did DSPC/Chol liposomes.

The increased levels of vincristine remaining in circulation in the plasma using SM-based liposomal formulations (FIG. 4) was reflected in greater amounts of vincristine loaded to P388 tumors (FIG. 6). This relationship suggests, for P388 tumors in BDF1 mice, that liposomes containing DSPC, SM and/or PEG-PE are not significantly different in their ability to extravasate from circulation to the peritoneal tumor.

EXAMPLE IV

In Vivo Efficacy of Liposomal Vincristine Against P388 Tumors

To determine whether increased delivery of vincristine to P388 tumors by SM/Chol and SM/Chol/PEG-PE liposomes, as shown in Example III, resulted in increased anti-tumor activity, the efficacy of liposomal formulations of vincristine was determined.

BDF1 mice bearing P388 tumors were treated with liposomal formulations of DSPC/Chol (55/45) mol/mol), SM/Chol (55/45, mol/mol) or SM/Chol/PEG-PE (55/40/5, mol,mol,mol) containing vincristine at a drug/lipid ratio of 0.1 (wt/wt).

Large unilamellar liposomes of DSPC/Chol (55/45), SM/Chol (55/45) and SM/Chol/PEG-PE (55/40/5) were prepared as described above and loaded with vincristine at a vincristine/lipid ratio of 0.1/1 (wt/wt). Liposomal vincristine was injected i.v. into BDF1 mice that had been administered 24 hours earlier with an i.p. injection of $10^6$P388 cells. Liposome concentration was adjusted to achieve vincristine dosages of 1.0, 2.0 and 4.0 mg/kg, then animal weights and survival was followed during the subsequent 60 days. Animals surviving for 60 days were re-injected with $10^6$P388 cells to evaluate the immune component of long-term survival.

Figure 7A:
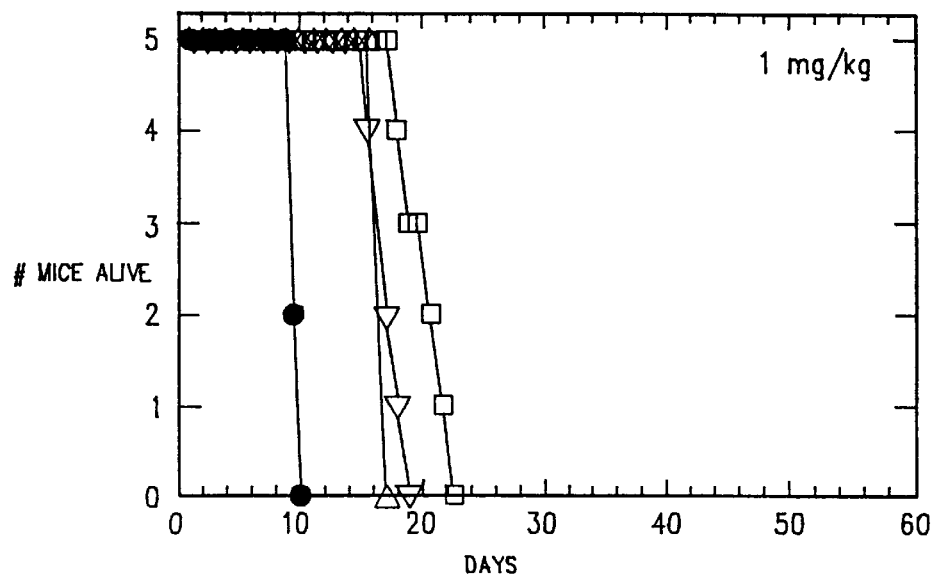
FIGS. 7A–7C show collectively the anti-tumor efficacy of liposomal formulations of vincristine. BDF1 mice containing P388 tumors were injected with large unilamellar liposomes of DSPC/Chol (55/45, mol/mol) (▽), SM/Chol (55/45, mol/mol) (□) or SM/Chol/PEG-PE (55/40/5, mol/mol/mol) (△) containing vincristine at a drug/lipid ratio of 0.1 (wt/wt). Control mice received no injection (●). Liposome concentrations prior to injection were adjusted to achieve vincristine dosages of 1.0 (FIG. 7A), 2.0 (FIG. 7B) and 4.0 (FIG. 7C) mg/kg.
Figure 7B:
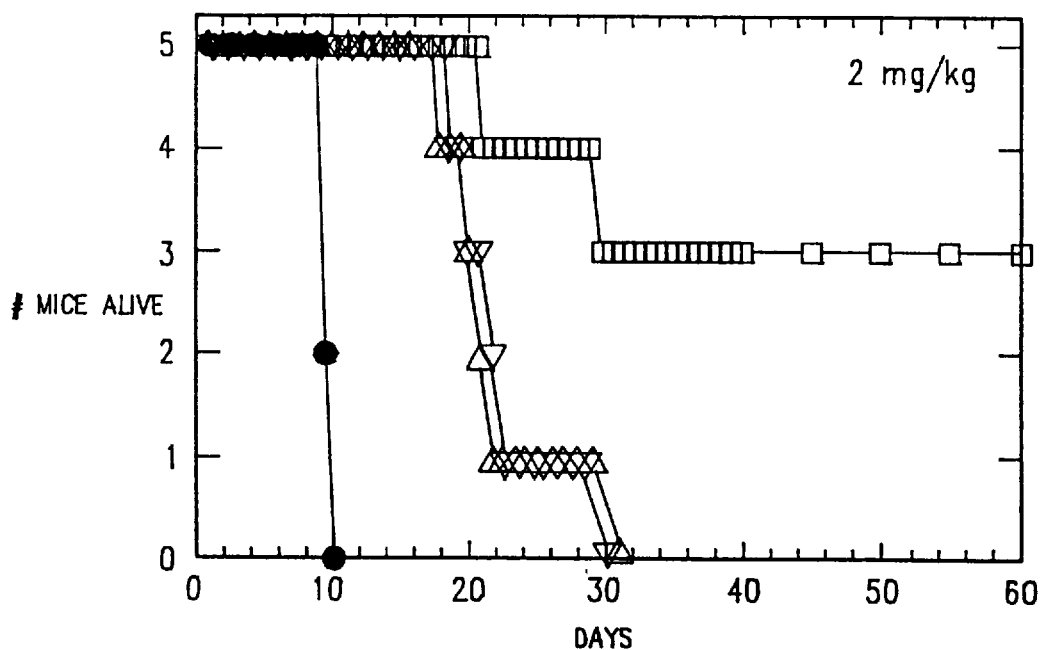
Figure 7C:
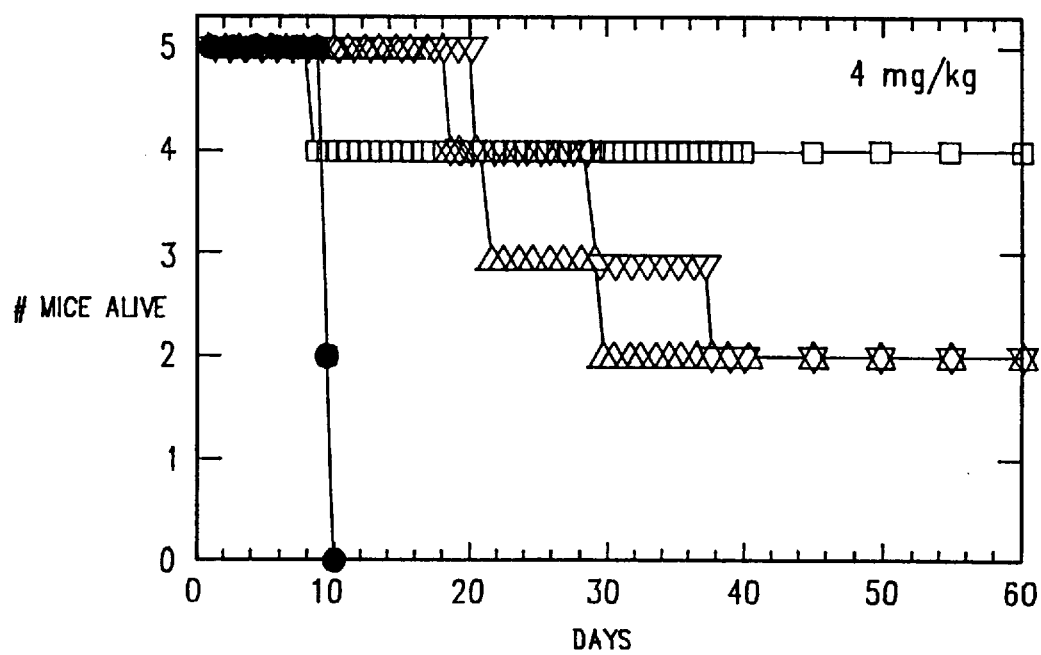

As shown in FIG. 7, control mice that received no injection of liposomal vincristine survived 10–11 days after administration of the P388 tumor. Treatment with either DSPC/Chol or SM/Chol/PEG-PE formulations at a vincristine dosage of 1 mg/kg increased the survival time to 17 and 19 days, respectively. Treatment with SM/Chol formulations at the same vincristine dosage gave a slight improvement in survival, 23 days.

At a vincristine dosage of 2 mg/kg, both DSPC/Chol and SM/Chol/PEG-PE formulations increased survival to 30–31 days. In contrast, at this vincristine dosage, the SM/Chol formulation was significantly more effective; 60% of the mice were surviving at 60 days after administration of the P388 tumor (FIG. 7). At a vincristine dosage of 4 mg/kg, both the DSPC/Chol and SM/Chol/PEG-PE formulations gave 40% of the mice surviving at 60 days after P388 tumor injection. Formulations of SM/Chol were significantly more efficacious; apart from a single vincristine toxicity death, survival of the remaining mice at 60 days was 100% (FIG. 7).

Thus, the antitumor efficacy of SM/Chol liposomes was significantly better than that of SM/Chol/PEG-PE liposomes (FIG. 7) despite the observation that the loading of vincristine to P388 tumors was identical in these two liposomal formulations (FIG. 6). This result suggests that the better vincristine retention properties of SM/Chol liposomes in circulation, compared to SM/Chol/PEG-PE liposomes (FIG. 3), may also occur in the peritoneal cavity and result in improved vincristine uptake by the P388 tumor cells. Formulations of SM/Chol were approximately two-fold more effective than were the formulations based on either DSPC/Chol or SM/Chol/PEG-PE. That is, survival achieved by DSPC/Chol and SM/Chol/PEG-PE formulations at vincristine dosages of 2.0 mg/kg were attained by SM/Chol at a dosage of 1.0 mg/kg. Similarly, the survival obtained by DSPC/Chol and SM/Chol/PEG-PE at a dose of 4.0 mg/kg of vincristine was very similar to that achieved by SM/Chol formulations at 2.0 mg/kg.

EXAMPLE V

Bioavailability of Liposomal Swainsonine

Female Balb/c mice, 5–6 weeks of age, were housed under standard conditions. The animals received free access to both food and water throughout the experiment after a one week acclimatization period prior to experimental manipulation. Swainsonine (Toronto Res. Chem.) was radiolabeled with tritium. Tritiated swainsonine was administered as a lipid-based formulation (L-Im) and as an aqueous formulation containing the free drug (F-Im). Tritiated swainsonine was loaded into sphingomyelin/cholesterol (Avanti Polar Labs) sphingosomes using a citrate buffer pH 2 gradient at a drug-to-lipid ratio of 0.2:1 (mol:mol) and with an efficiency of loading of 80%. Two hundred microliters of the lipid and aqueous swainsonine formulations were given orally by gavage (p.o.), intraperitoneally (i.p.), or intravenously (i.v.). Fifty microliter blood samples were collected by retroorbital bleeds at 1, 3, 6, and 24 hours after administration. The blood samples were bleached and then counted in a scintillation counter. Results were expressed as the percentage of the administered dose in the blood at various time-points after administration.

Figure 8:
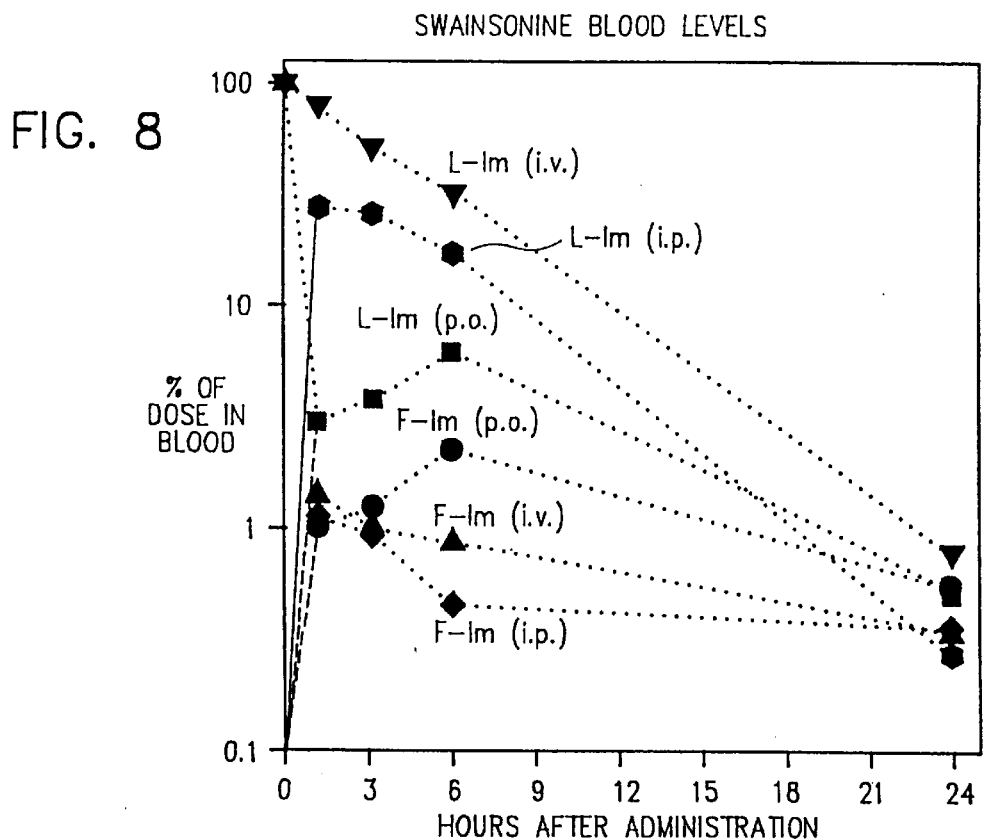
FIG. 8 shows blood levels of radiolabeled swainsonine in Balb/c mice administered as either a liposomal formulation (L-Im) or as an aqueous solution of the free drug (F-Im). Formulations were administered orally by gavage (p.o.), intraperitoneally (i.p.), or intravenously (i.v.). Blood was removed at 1 hr., 3 hr., 6 hr., and 24 hrs. after the dose.

As seen in FIG. 8, the liposomal formulation (L-Im) of swainsonine has superior bioavailability and achieves higher blood levels when compared to the free aqueous formulation (F-Im). The oral bioavailability of swainsonine is about 60–65% when compared to swainsonine administered intravenously.

EXAMPLE VI

Efficacy of Swainsonine and GM-CSF

Female C57BL/6 mice (average weight 15.03 g), were used and housed under standard conditions. The animals received free access to both food and water throughout the experiment after a one week acclimatization period prior to experimental manipulation. The mice were 6 weeks old on the beginning of the experiment and placed randomly in 12 groups of 5 mice per group. Forty mice were given a single bolus (i.p.) injection of either methotrexate (Mtx, 410 mg/kg) (Sigma Chemical Co.) or Doxorubicin (Dox, 14.9 mk/kg) (Adria Laboratories). Two days after chemotherapy, administration of swainsonine (2 mg/kg i.p. or p.o.), recombinant murine GM-CSF (granulocyte macrophage-colony stimulating factor) (1 µg/mouse/day i.p., $5 \times 10^4$ U/µg activity) (R & D Systems) or phosphate buffered saline (PBS) (200 µl i.p.) was provided for 10 consecutive days (once per day). The number of deaths was recorded for each treatment group over an observation period of 14 days.

Results in Table I (below) show that when swainsonine is administered for 10 days after a $LD_{50}$ dose of chemotherapeutic (Mtx or Dox), all animals administered swainsonine intravenously or by i.p. handled the cytotoxic insult and survived beyond 2 weeks after chemotherapy. Half of the animals treated with Mtx and half treated with Dox died within a few days after chemotherapy. Animals treated with an i.p. administration of recombinant murine GM-CSF for 10 days did not do as well as with swainsonine; about half of the animals treated with Mtx died within a few days after initiation of the 10 day dosing period. Animals dosed with Dox and 10 days of GM-CSF survived the two week recovery period. Swainsonine was administered orally for 10 days to the chemotherapeutic-treated animals and all but one animal (in the Mtx-treated group) survived the cytotoxic treatment.

TABLE I

| Test Agent | Administration | Survival (%) |
|---|---|---|
| 1. PBS | i. p. | 100 |
| 2. MTX | i. p. | 40 |
| 3. DOX | i. p. | 60 |
| 4. L-SW | i. p. | 100 |

TABLE I-continued

| Test Agent | Administration | Survival (%) |
|---|---|---|
| 5. MTX/L-SW | i. p. | 100 |
| 6. DOX/L-SW | i. p. | 100 |
| 7. GM-CSF | i. p. | 100 |
| 8. MTX/GM-CSF | i. p. | 60 |
| 9. DOX/GM-CSF | i. p. | 100 |
| 10. L-SW | p. o. | 100 |
| 11. MTX/L-SW | p. o. | 80 |
| 12. DOX/L-SW | p. o. | 100 |

EXAMPLE VII

Recovery from Chemotherapeutic Induced Leukopenia

Figure 9:
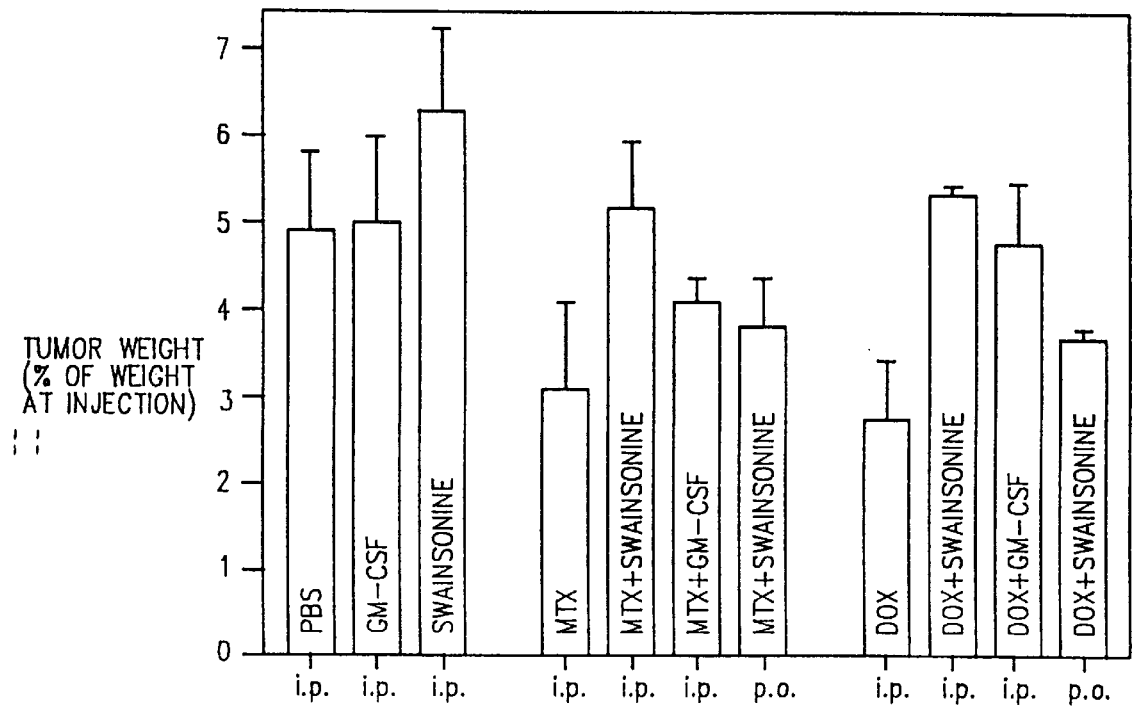
FIG. 9 shows the effects of GM-CSF and swainsonine on bone marrow cellularity 14 days after chemotherapeutic administration to C57BL/6 mice.

On the 15th day after the initial chemotherapeutic dose, 4 mice from each group of the immunomodulation study (Example 6) were randomly sacrificed and up to 1 ml of blood was obtained by cardiac puncture. Circulating peripheral WBCs were counted, blood smears (for neutrophil counts) were made and plasma samples were collected and tested for cytokine production (IL-1, IL-2, TNF). Blood cytokine levels (TNF, IL-1, and IL-2) were assayed by commercially available assay kits. The spleen, thymus and bone marrow were removed and single cell suspensions were prepared. The cellularity of these lymphoid organs was assessed by trypan blue exclusion test. FIG. 9 shows the effects of GM-CSF and swainsonine on the bone marrow cellularity at 14 days after chemotherapy drug administration. As shown, swainsonine, given orally or by i.p. administration performed as effectively as GM-CSF given by i.p. for 10 consecutive days.

Figure 10A:
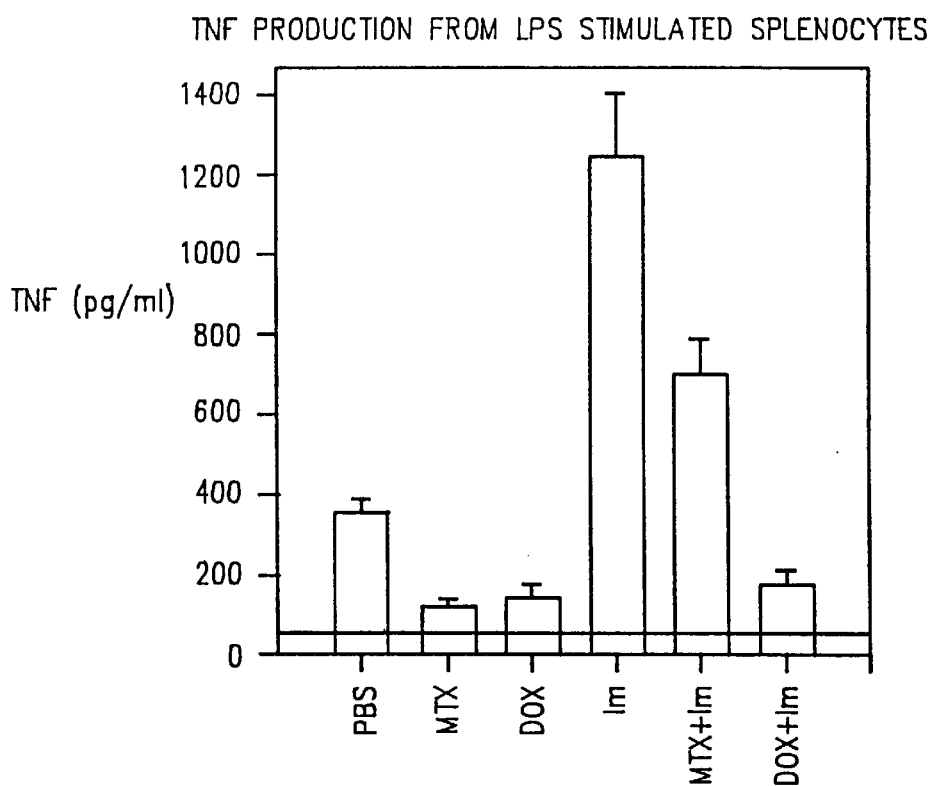
FIGS. 10A and 10B illustrate, respectively, TNF production from LPS stimulated splenocytes, and IL-2 production from ConA stimulated splenocytes, collected from C57BL/6 mice 14 days after chemotherapeutic treatment.
Figure 10B:
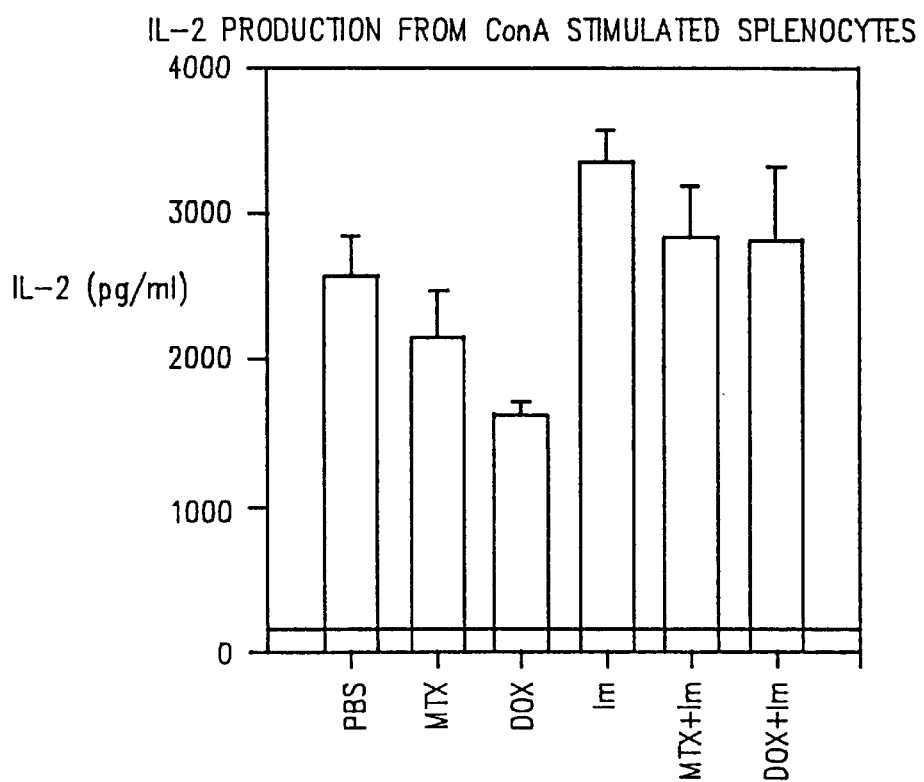

Cells from spleen, thymus and bone marrow were tested for their ability to respond to stimulation from different mitogens: ConA (1, 2.5 and 5 µg/ml) (Sigma), phytohemagglutinin (PHA) (1, and 2.5 µg/ml) (Sigma) and LPS (2.5 and 5 µg/ml) (Difco). After 72 hours of stimulation the proliferative response was measured using CellTiter 96 (Promega). Simultaneously, mitogen stimulated splenocytes were set up for cytokine production after ConA (2.5 µg/ml) and lipopolysaccharide (LPS) (2.5 µg/ml) stimulation. The supernatants were collected after 24 hr. and 48 hr. and tested for Tumor Necrosis Factor-α (TNF-α) and Interleukin-2 (IL-2) production using the direct ELISA method. Supernatants from unstimulated cells served as controls. Results are expressed as pg/ml of TNF-α (sensitivity of the assay is <25 pg/ml) or IL-2 (sensitivity of the assay is <3 pg/ml). As shown in FIGS. 10A and 10B, respectively, TNF and IL-2 levels in ConA and LPS stimulated splenocytes were significantly elevated in swainsonine-treated animals compared to chemotherapy-treated and PBS (no treatment) controls.

To establish an advantage for the oral route of administration, swainsonine was incubated in vitro in simulated gastric contents for various periods of time (1, 2, 4, 24, 48 and 72 hrs.) and the "oral stability" of swainsonine was determined. Swainsonine was also incubated in hydrochloric acid (pH2) containing the main gastric digestive enzyme, pepsin. The in vitro stability tests have shown swainsonine to be stable under these harsh conditions for up to 72 hours.

EXAMPLE VIII

Figure 11A:
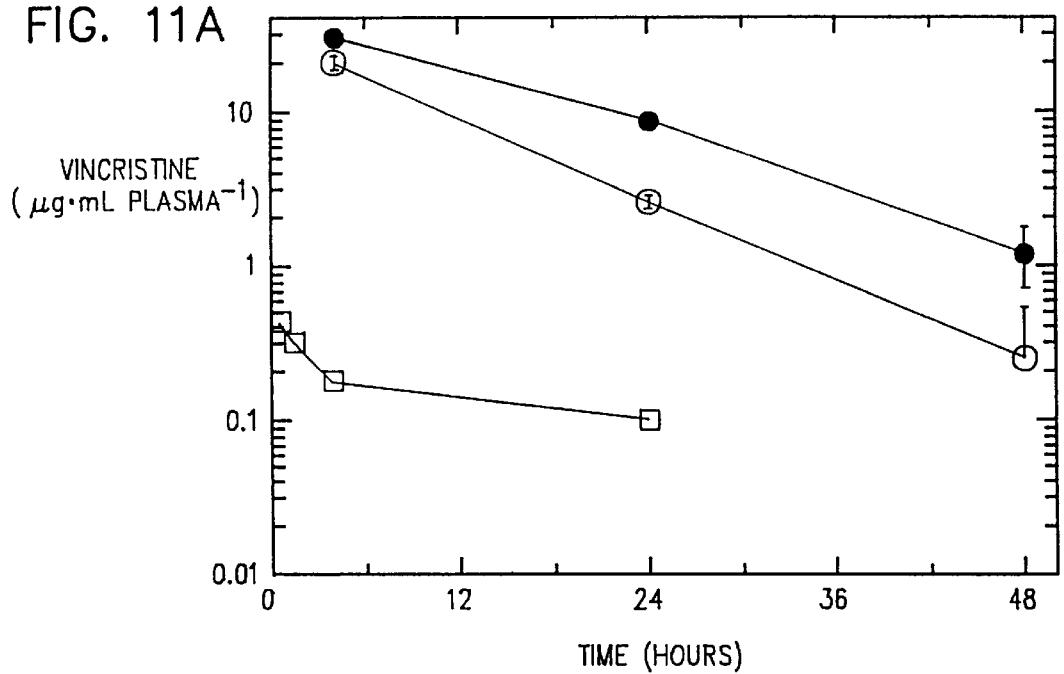
FIGS. 11A and 11B show vincristine levels in (A) plasma and (B) tumors after administration of free and liposomal vincristine in SCID mice bearing A431 tumors. SCID mice bearing two A431 tumors were injected i.v. with free vincristine (□) or with large unilamellar liposomes of DSPC/Chol (○) or SM/Chol (●) containing vincristine at a drug/lipid ratio of 0.1 (wt/wt). Vincristine was injected at a dose of 2.0 mg/kg, representing a lipid of dose of 20 mg/kg. Data represent means (±standard error) of three mice (6 tumors); where standard error bars are not visible, they are smaller than the size of the symbol.

Pharmacokinetics, Tumor Loading and Therapy in SCID Mice Bearing A431 Tumors Tumor loading and antitumor efficacy properties of DSPC/Chol and SM/Chol liposomal formulations of vincristine were determined in mice bearing solid human A431 squamous cell xenograft tumors. These experiments were undertaken to ensure that the positive results observed in the murine ascitic P388 tumor model were representative of other tumor types. SCID mice bearing 100–200 mg solid human A431 tumors were injected i.v. with free vincristine or with liposomes of either DSPC/Chol or SM/Chol containing vincristine. Vincristine encapsulated DSPC/Chol and SM/Chol liposomes were prepared as in Example II. Encapsulation of vincristine in DSPC/Chol and SM/Chol liposomes increased the amount of vincristine remaining in circulation 24 hours after administration by 28- and 87-fold, respectively, compared with free vincristine (FIG. 11A). As observed in BDF1 mice bearing P388 tumors, the amount of vincristine remaining in the circulation in SM/Chol liposomes at 24 hours after injection was approximately 3-fold greater than for vincristine encapsulated in DSPC/Chol liposomes (FIG. 11A).

Figure 11B:
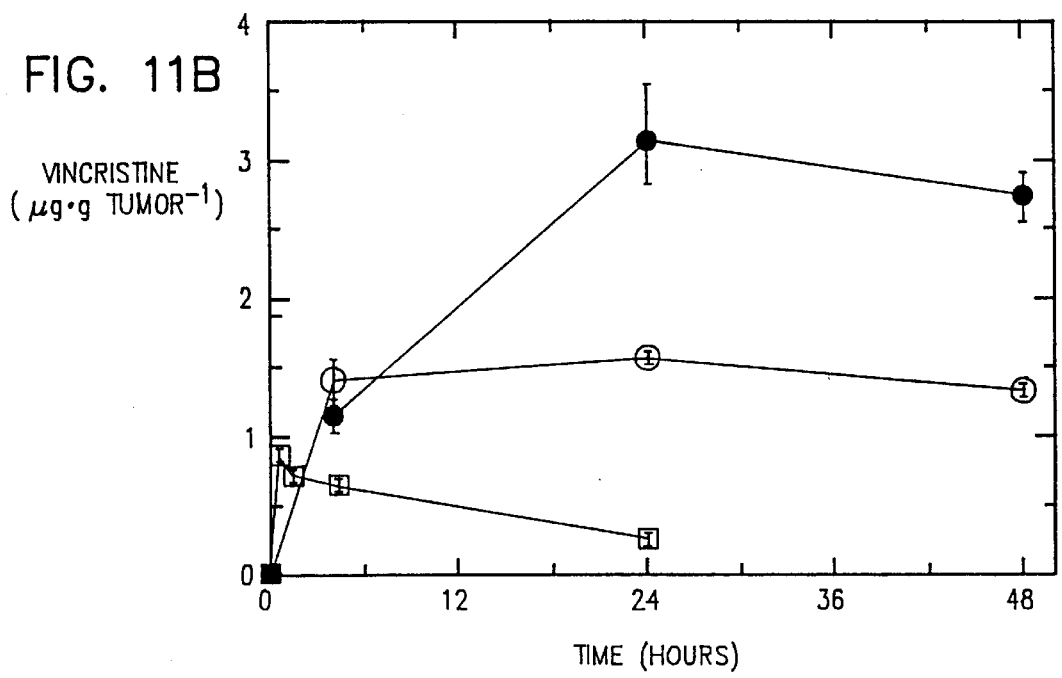

Improved vincristine circulation longevity correlated with increases in the loading of vincristine in the A431 tumors (FIG. 11A). Specifically, free vincristine levels in the A431 tumors were highest (0.856 mg/g tumor) at 0.5 hours after injection and decreased to 0.32 mg/g tumor at 24 hours (FIG. 11B). Encapsulation of vincristine in DSPC/Chol liposomes increased the amount of vincristine in A431 tumors at 4 to 48 hours after administration to 1.3–1.55 mg/g tumor, respectively (FIG. 11B). Encapsulation of vincristine in SM/Chol liposomes resulted in a further increase in vincristine delivery to A431 tumors at 24 to 48 hours after injection to 2.8–3.2 mg/g tumor, representing a 2-fold increase in the delivery obtained with DSPC/Chol liposomes. As observed in the murine ascitic tumor model, the vincristine/lipid observed in the solid human A431 tumors were very similar to those observed in the plasma. That is, for vincristine encapsulated in DSPC/Chol liposomes, the vincristine/lipid (wt/wt) ratios at 24 hours after injection were 0.022 in the plasma and 0.029 in the tumor, while for vincristine encapsulated in SM/Chol liposomes the vincristine/lipid ratios were 0.055 in the plasma and 0.050 in the tumor.

Figure 12:
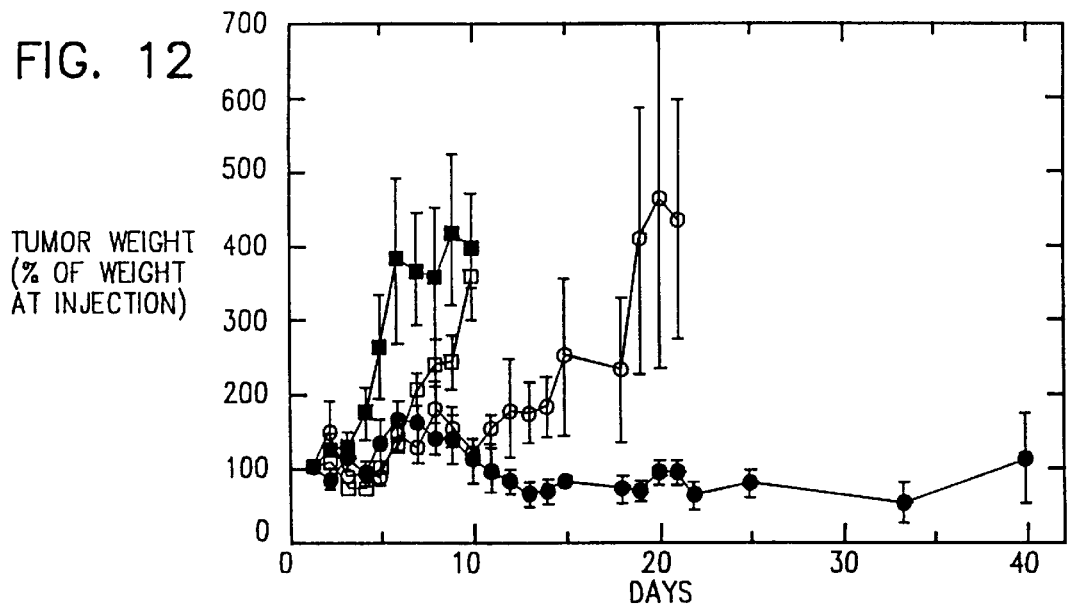
FIG. 12 shows antitumor efficacy of free and liposomal vincristine in SCID mice bearing A431 tumors. SCID mice bearing two A431 tumors received no treatment (■) or were injected i.v. with free vincristine (□) or with large unilamellar liposomes of DSPC/Chol (○) or SM/Chol (●) containing vincristine at a drug/lipid ratio of 0.1 (wt/wt). Vincristine was injected at a dose of 2.0 mg/kg, representing a lipid of dose of 20 mg/kg. Data represent the weight of A431 tumors (expressed as the percent of the tumor weight immediately prior to treatment) and are the means (±standard error) of 8–10 tumors in 4–5 mice.
Figure 13:
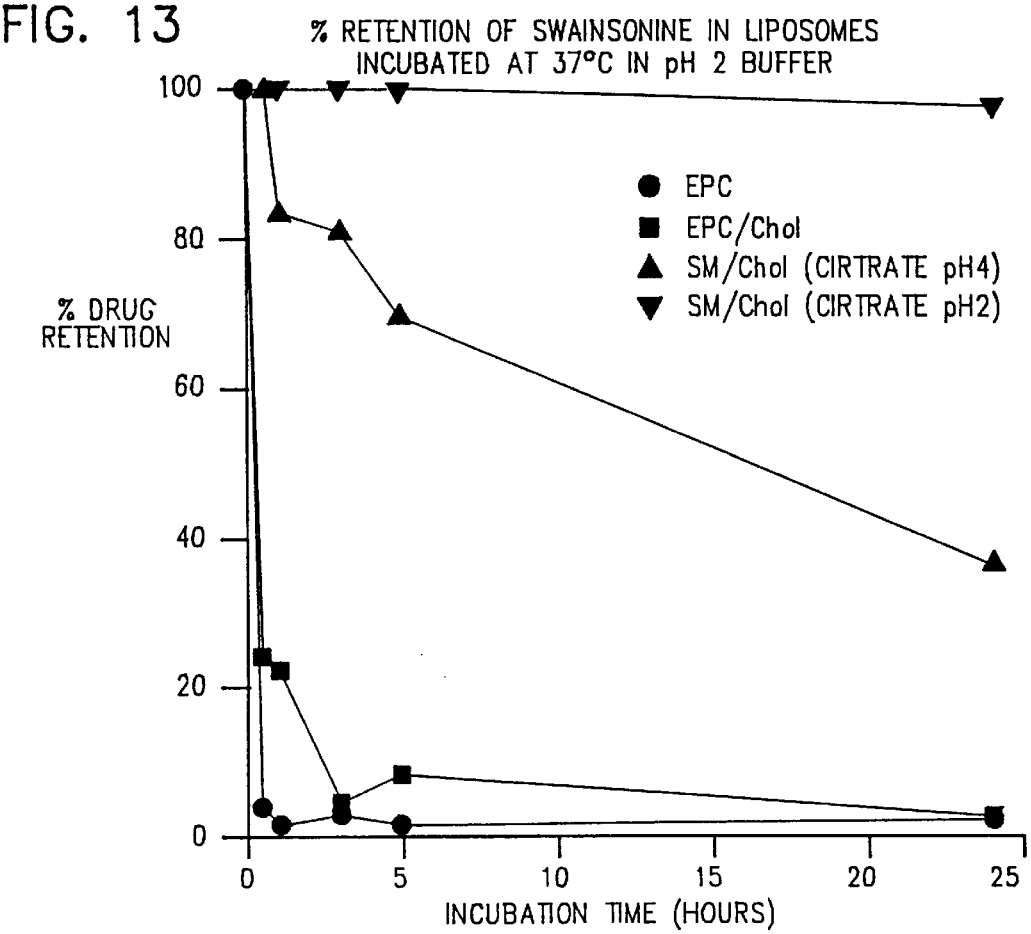
FIG. 13 shows the percent retention over time of swainsonine in liposomes incubated at 37° C. at pH 2. Swainsonine was loaded into liposomes at a drug to lipid ratio of 0.2/1.0 (mol/mol) using 0.3M citrate pH 4 (except SM/Chol at pH 2). EPC, egg phosphotidyl choline; EPC/Chol, egg phosphotidyl choline/cholesterol (55%/45%) (mol/mol); SM/Chol, sphingomyelin/cholesterol (55%/45%) (mol/mol).
Figure 14:
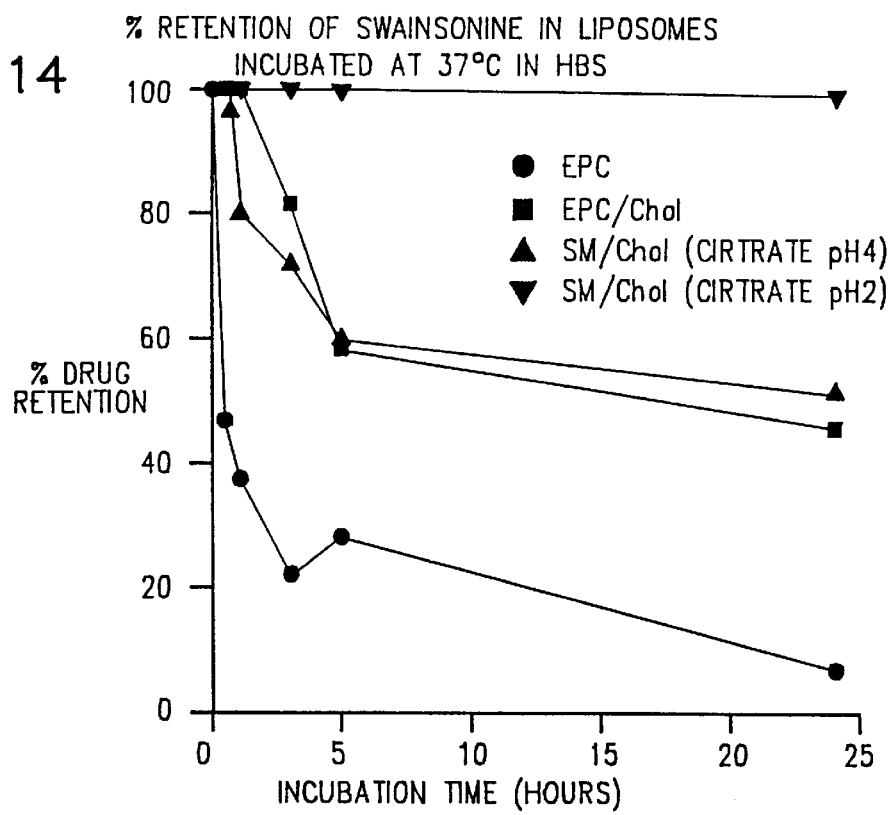
FIG. 14 shows the percent retention over time of swainsonine in liposomes incubated at 37° C. in HEPES buffered saline (HBS) pH 7.5.
Figure 15:
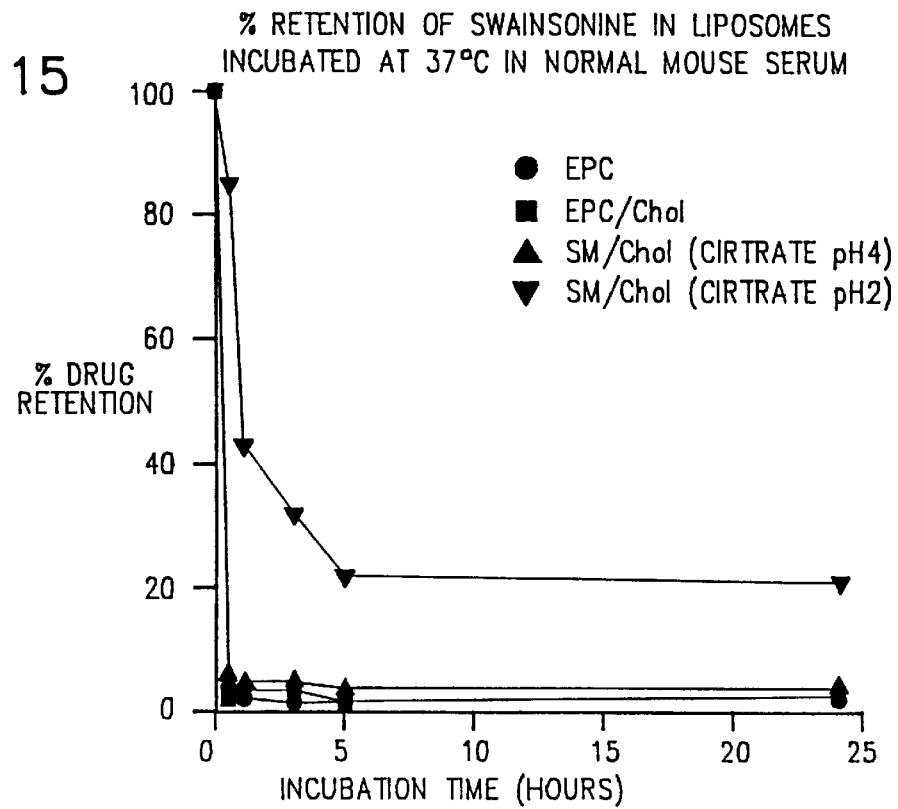
FIG. 15 shows the percent retention over time of swainsonine in liposomes incubated at 37° C. in normal mouse serum.

The antitumor efficacy of free and liposomal vincristine against A431 was closely correlated with vincristine accumulation at the tumor site (FIG. 12). SCID mice bearing the A431 tumors that received no treatment showed a 100% increase in tumor weight within 4–5 days after treatment was initiated and required termination within 10 days when the tumor exceeded 10% of the total body weight. Tumor bearing SCID mice treated with free vincristine at 2.0 mg/kg had a brief delay in tumor growth (100% increase in tumor weight achieved within 6–8 days) but required termination between 10–12 days. In contrast, treatment with vincristine encapsulated in DSPC/Chol liposomes resulted in a significant delay in tumor growth (100% increase in tumor weight at 15–20 days, termination at 21 days after treatment). This therapy was further enhanced by a single treatment of vincristine encapsulated in SM/Chol liposomes. In this treatment group a small but consistent decrease in tumor size was observed. At 15 days after injection, several tumors were palpable but unmeasurable and by 33 days after treatment several tumors were not palpable. Of the five mice (total of 10 tumors) treated with SM/Chol liposomal vincristine, 1 animal was terminated early due to tumor ulceration, not due to tumor growth. Of the eight tumors remaining at 40 days after liposome injection, histological analysis indicated that all eight tumors were actively dividing squamous cell carcinomas of a mass undetectable by physical examination. Therefore, treatment with SM/Chol liposomal vincristine effected a significant reduction in tumor growth, although none of the original tumors were cured.

EXAMPLE IX

Pharmacokinetics and Biodistribution of Intratracheal Ciprofloxacin Administration A concentration gradient was formed across SM/Chol (55/45 mol/mol), DPPC (diplamitoylphosphatidylcholine)/Chol (55/45 mol/mol), and DSPC/Chol (55/45 mol/mol) liposomal vesicles (0.1 μm) by formation of the vesicles in 300 mM methylammonium sulfate followed by dialysis against physiological saline. Ciprofloxacin (cipro) was subsequently loaded into liposomes at 0.3:1 (mol drug:mol lipid) at a temperature of 50° to 65° C. Liposomes and free ciprofloxacin were administered intratracheally (i.t.) as droplets via an intratracheal catheter to CD1 mice at a dose of 15 mg/kg. Lipid, ciprofloxacin, and ciprofloxacin/lipid ratios in lung were determined over time using radiolabelled $^{14}$C-ciprofloxacin and $^3$H-CHDE (cholesteryl-4-hexadecyl ether).

At all times between 15 minutes and 24 hours after intratracheal administration of either free or liposomal ciprofloxacin, the levels of ciprofloxacin in the plasma were not detectable. Similarly, liposomal carriers were not detectable in the plasma at any time after intratracheal administration. Rather, free ciprofloxacin was rapidly released from the lung to the circulation and subsequently cleared from circulation. In contrast, liposomal formulations which were retained in the lung slowly released ciprofloxacin. Lipid amounts in the lung were typically stable over 24 hours at 80% of the administered dose of lipid (Table II). Ciprofloxacin levels in the lung decreased over 24 hours (Table III) as a consequence of leakage from liposomes in the lung as indicated by the decrease in ciprofloxacin/lipid ratio during liposome residency in the pulmonary tissue (Table IV).

TABLE II

CIPROFLOXACIN LEVELS IN THE LUNG AFTER INTRATRACHEAL ADMINISTRATION

| Time (hrs) after administration | Free cipro i.t. (μg/g wet tissue) | DPPC/Chol cipro i.t. (μg/g wet tissue) | DSPC/Chol cipro i.t. (μg/g wet tissue) | SM/Chol cipro i.t. (μg/g wet tissue) |
|---|---|---|---|---|
| 0.25 | 120.11 ± 31.32 | | | |
| 0.50 | 36.62 ± 16.47 | | | |

TABLE II-continued

CIPROFLOXACIN LEVELS IN THE LUNG AFTER INTRATRACHEAL ADMINISTRATION

| Time (hrs) after administration | Free cipro i.t. (µg/g wet tissue) | DPPC/Chol cipro i.t. (µg/g wet tissue) | DSPC/Chol cipro i.t. (µg/g wet tissue) | SM/Chol cipro i.t. (µg/g wet tissue) |
|---|---|---|---|---|
| 1.00 | 9.37 ± 0.82 | 981.39 ± 107.89 | 392.15 ± 382.16 | 1069.45 ± 49.38 |
| 4.00 | | 701.53 ± 188.27 | 885.39 ± 98.52 | 805.36 ± 327.36 |
| 6.00 | | 895.94 ± 28.01 | 729.49 ± 188.72 | 627.84 ± 335.57 |
| 24.00 | | 102.89 ± 72.99 | 329.73 ± 19.20 | 477.45 ± 151.76 |

TABLE III

LIPID LEVELS IN THE LUNG AFTER INTRATRACHEAL ADMINISTRATION

| Time (hrs.) after administration | DPPC/Chol cipro i.t. (µg/g wet tissue) | DSPC/Chol cipro i.t. (µg/g wet tissue) | SM/Chol cipro i.t. (µg/g wet tissue) |
|---|---|---|---|
| 1.00 | 6657 ± 749 | 2593 ± 2519 | 6265 ± 239 |
| 4.00 | 5976 ± 1355 | 6740 ± 684 | 5411 ± 2056 |
| 6.00 | 7592 ± 161 | 6379 ± 1413 | 4486 ± 2335 |
| 24.00 | 5044 ± 1201 | 7174 ± 172 | 5898 ± 1450 |

TABLE IV

DRUG TO LIPID RATIOS IN THE LUNG AFTER INTRATRACHEAL ADMINISTRATION

| Time (hrs) after Administration | DPPC/Chol cipro i.t. (µg cipro/µg lipid) | DSPC/Chol cipro i.t. (µg cipro/µg lipid) | SM/Chol cipro i.t. (µg cipro/µg lipid) |
|---|---|---|---|
| 0 | 0.18 | 0.18 | 0.19 |
| 1.0 | 0.15 | 0.15 | 0.17 |
| 2.0 | 0.12 | 0.13 | 0.15 |
| 4.0 | 0.12 | 0.11 | 0.14 |
| 24.0 | 0.02 | 0.05 | 0.08 |

As observed after intravenous administration of the different liposomal formulations, the retention of ciprofloxacin decreased in the sequence SM/Chol>DSPC/Chol~DPPC/Chol. Plasma levels of ciprofloxacin after intratracheal administration of either free ciprofloxacin or lipsomal formulations are identical and are negligible. These levels are identical to intravenous administration of free ciprofloxacin. Ciprofloxacin levels in the lung are approximately 100-fold greater in the liposomal formulations compared to free ciprofloxacin at all times between one hour and four hours after administration. This is a consequence of the inability of liposomes administered via the intratracheal route to escape to the circulation and the retention of ciprofloxacin in these liposomes.

EXAMPLE X

Pharmacokinetics & Biodistribution of I.V. vs. I.P. Administration

Liposomal (SM/Chol) ciprofloxacin, prepared as in Example IX, and free ciprofloxacin were administered by i.v. and i.p. to CD1 mice at 15 mg/kg. As shown in Table V, no difference was observed in the plasma ciprofloxacin levels after i.v. or i.p. administration of the free antibiotic. However, encapsulation of ciprofloxacin in SM/Chol liposomes significantly increased the plasma ciprofloxacin.

TABLE V

PLASMA CLEARANCE OF CIPROFLOXACIN WHEN ADMINISTERED IV AND IP

| Time (hrs.) after administration | Free cipro i.v. (µg/100 µl plasma) | Free cipro i.p. (µg/100 µl plasma) | SM/Chol cipro i.v. (µg/100 µl plasma) | SM/Chol cipro i.p. (µg/100 µl plasma) |
|---|---|---|---|---|
| 0.25 | 0.35 ± 0.005 | 0.43 ± 0.01 | | |
| 0.50 | 0.20 ± 0.03 | 0.18 ± 0.09 | | |
| 1.00 | 0.11 ± 0.02 | 0.07 ± 0.05 | 7.38 ± 0.18 | 2.79 ± 0.16 |
| 4.00 | 0.05 ± 0.001 | 0.06 ± 0.007 | 4.87 ± 0.39 | 4.23 ± 0.32 |
| 6.00 | 0.03 ± 0.001 | | 2.09 ± 0.89 | 2.71 ± 0.73 |
| 24.00 | | | 0.02 ± 0.003 | 0.02 ± 0.006 |

Plasma levels of liposomal ciprofloxacin were maximal at four hours after i.p. administration, compared to maximal 1 hour after i.v. administration. This difference is likely due to a four hour time lag required for drainage of the liposomes from the peritoneal cavity to the circulation via the lymphatic system. This conclusion is supported by the observation that the plasma lipid concentrations (Table VI) follow the identical pattern of accumulation as observed for liposomal ciprofloxacin (Table V).

TABLE VI

PLASMA CLEARANCE OF LIPOSOMES WHEN ADMINISTERED I.V. AND I.P.

| Time (hrs.) after administration | SM/Chol cipro i.v. ($\mu$g/100 $\mu$l plasma) | SM/Chol cipro i.p. ($\mu$g/100 $\mu$l plasma) |
|---|---|---|
| 1.00 | 46.44 ± 0.49 | 17.40 ± 1.15 |
| 4.00 | 36.35 ± 3.14 | 34.45 ± 2.09 |
| 6.00 | 23.23 ± 9.39 | 25.48 ± 5.57 |
| 24.00 | 0.22 ± 0.02 | 0.17 ± 0.10 |

This indicates that the liposomes containing ciprofloxacin are leaving the peritoneal cavity and accumulating in circulation, rather than the liposomes leaking ciprofloxacin in the peritoneal cavity and the free ciprofloxacin accumulating in the blood. This interpretation is supported by the observation that the ciprofloxacin/lipid ratios in the plasma are very similar after i.v. and i.p. administration (Table VII).

TABLE VII

DRUG TO LIPID RATIOS IN PLASMA

| Time (hrs.) after Administration | SM/Chol cipro i.v. ($\mu$g cipro/$\mu$g lipid) | S/M Chol ($\mu$g cipro/$\mu$g lipid) |
|---|---|---|
| 1.00 | 0.16 ± 0.003 | 0.16 ± 0.002 |
| 4.00 | 0.13 ± 0.008 | 0.13 ± 0.002 |
| 6.00 | 0.09 ± 0.008 | 0.11 ± 0.01 |
| 24.00 | 0.10 ± 0.03 | 0.10 ± 0.04 |

After the i.v. or i.p. administration of liposomal and free ciprofloxacin, the accumulation of ciprofloxacin in the liver, spleen and lung was examined. In all three tissues, administration of ciprofloxacin in the liposomal form significantly increased the total amount of ciprofloxacin accumulating in the tissues using either the i.v. or i.p. routes of administration. However, there were no significant differences in tissue ciprofloxacin levels between i.v. and i.p. routes of administration of liposomal ciprofloxacin at greater than four hours after administration. Thus, the pharmacokinetics of free ciprofloxacin are identical after i.p. or i.v. administration; the pharmacokinetics of SM/Chol formulations of ciprofloxacin are identical at greater than four hours after i.p. and i.v. administration; and, the accumulation of ciprofloxacin-loaded SM/Chol liposomes in the liver and spleen is lower after i.p. administration than after i.v. administration. However, accumulation of these liposomes in the lung after i.p. or i.v. administration is identical at greater than four hours after administration.

EXAMPLE XI

Longevity of Liposomal Ciprofloxacin

To evaluate the effect of liposomal encapsulation on the circulation longevity of ciprofloxacin, ciprofloxacin labelled with $^{14}$C-ciprofloxacin was loaded into liposomes of DPPC/cholesterol, DSPC/cholesterol or SM/cholesterol as described in Example IX. Liposomes were labelled with the non-metabolized lipid radiotracer $^3$H-cholesterylhexadecyl ether. Each liposomal ciprofloxacin formulation, and free ciprofloxacin was administered i.v. via tail vein injection into 12 CD1 mice at a dose of 15 mg ciprofloxacin/kg. At various times after i.v. administration, mice were anesthetized, blood recovered by cardiac puncture into EDTA-Microtainer tubes, and the plasma isolated by centrifugation. Tissue were also recovered and homogenized. Both lipid and ciprofloxacin were assayed by liquid scintillation counting of the plasma and tissue homogenates. Results of the ciprofloxacin pharmacokinetics are shown in Table VIII. Estimation of the ciprofloxacin half-life in plasma after i.v. administration was done by calculating the rate constant for ciprofloxacin clearance from the slope of the ln [ciprofloxacin] vs. time plots. The half-life for ciprofloxacin increased from approximately 0.2 hours for the free drug to greater than 3 hours for all liposomal formulations. This represents at least a 15-fold increase in the circulation lifetime of ciprofloxacin as a consequence of encapsulation in liposomes. Analysis of the drug/lipid ratios in plasma (Table IX) indicate that retention of encapsulated ciprofloxacin in liposomes was best with the SM/chol liposomal formulation. This result is the likely cause of increased ciprofloxacin accumulation in tissues such as the spleen (Table X), kidney (Table XI) and lung (Table XII) using the SM/Chol liposomal formulation when compared to both the DSPC/Chol and DPPC/Chol liposomal formulations as well as compared to free ciprofloxacin.

TABLE VIII

CIPROFLOXACIN LEVELS IN PLASMA AFTER I.V. ADMINISTRATION

| Time (hrs.) after i.v. administration | Free Cipro ($\mu$g cipro/100 $\mu$L plasma) | DPPC/Chol ($\mu$g cipro/100 $\mu$L plasma) | DSPC/Chol ($\mu$g cipro/100 $\mu$L plasma) | SM/Chol ($\mu$g cipro/100 $\mu$L plasma) |
|---|---|---|---|---|
| 0.0833 | 0.5996 ± 0.0135 | | | |
| 0.25 | 0.4096 ± 0.0308 | | | |
| 0.5 | 0.2720 ± 0.0323 | | | |
| 1 | 0.1324 ± 0.0008 | 5.6299 ± 0.177 | 13.811 ± 0.379 | 10.97 ± 0.343 |
| 4 | | 1.3616 ± 0.162 | 4.009 ± 0.167 | 7.741 ± 0.408 |
| 6 | | 0.7236 ± 0.0186 | 2.309 ± 0.239 | 5.939 ± 0.238 |
| 24 | | 0.0330 ± 0.001 | 0.0461 ± 0.0006 | 0.0452 ± 0.002 |

TABLE IX

DRUG TO LIPID RATIOS IN THE PLASMA AFTER I.V. ADMINISTRATION

| Time (hrs.) after i.v. administration | DPPC/Chol ($\mu$g cipro/$\mu$g lipid) | DSPC/Chol ($\mu$g cipro/$\mu$g lipid) | SM/Chol ($\mu$g cipro/$\mu$g lipid) |
|---|---|---|---|
| 0 | 0.18 ± 0 | 0.178 ± 0 | 0.190 ± 0 |
| 1 | 0.0972 ± 0.0004 | 0.1079 ± 0.0015 | 0.1736 ± 0.0019 |
| 4 | 0.0262 ± 0.0019 | 0.0491 ± 0.0013 | 0.1364 ± 0.0029 |
| 6 | 0.0193 ± 0.0012 | 0.0311 ± 0.0013 | 0.1126 ± 0.0021 |
| 24 | 0.0563 ± 0.0173 | 0.0121 ± 0.0079 | 0.1095 ± 0.0289 |

TABLE X

CIPROFLOXACIN ACCUMULATION IN THE SPLEEN AFTER I.V. ADMINISTRATION

| Time (hrs.) after i.v. administration | Free cipro ($\mu$g cipro/g tissue) | DPPC/Chol ($\mu$g cipro/g tissue) | DSPC/Chol ($\mu$g cipro/g tissue) | SM/Chol ($\mu$g cipro/g tissue) |
|---|---|---|---|---|
| 0.0833 | 16.10 ± 0.191 | | | |
| 0.25 | 9.43 ± 0.76 | | | |
| 0.5 | 5.48 ± 0.294 | | | |
| 1 | 3.49 ± 0.271 | 105.1 ± 10.5 | 42.3 ± 2.55 | 94.6 ± 2.27 |
| 4 | | 56.0 ± 7.4 | 53.9 ± 11.1 | 89.0 ± 3.47 |
| 6 | | 25.8 ± 5.4 | 9.92 ± 2.73 | 65.7 ± 1.31 |
| 24 | | 0.0 ± 0.17 | 0.0 ± 0.09 | 0.0 ± 0.647 |

TABLE XI

CIPROFLOXACIN ACCUMULATION IN THE KIDNEY AFTER I.V. ADMINISTRATION

| Time (hrs.) after i.v. administration | Free cipro ($\mu$g cipro/g tissue) | DPPC/Chol ($\mu$g cipro/g tissue) | DSPC/Chol ($\mu$g cipro/g tissue) | SM/Chol ($\mu$g cipro/g tissue) |
|---|---|---|---|---|
| 0.0833 | 23.5 ± 2.55 | | | |
| 0.25 | 13.5 ± 1.47 | | | |
| 0.5 | 8.85 ± 1.37 | | | |
| 1 | 3.58 ± 0.25 | 10.54 ± 1.53 | 9.73 ± 0.54 | 9.64 ± 0.66 |
| 4 | | 1.07 ± 0.43 | 0.0 ± 0.42 | 9.07 ± 1.07 |
| 6 | | 0.0 ± 0.13 | 0.0 ± 0.31 | 7.12 ± 0.11 |
| 24 | | 0.0 ± 0.03 | 0.0 ± 0.05 | 0.0 ± 0.18 |

TABLE XII

CIPROFLOXACIN ACCUMULATION IN THE LUNG AFTER I.V. ADMINISTRATION

| Time (hrs.) after i.v administration | Free cipro ($\mu$g cipro/g tissue) | DPPC/Chol ($\mu$g cipro/g tissue) | DSPC/Chol. ($\mu$g cipro/g tissue) | SM/Chol ($\mu$g cipro/g tissue) |
|---|---|---|---|---|
| 0.0833 | 10.3 ± 0.09 | | | |
| 0.25 | 6.29 ± 0.22 | | | |
| 0.5 | 3.12 ± 0.35 | | | |
| 1 | 2.07 ± 0.29 | 8.66 ± 1.05 | 7.02 ± 1.14 | 12.0 ± 1.89 |
| 4 | | 0.24 ± 0.29 | 0.0 ± 0.37 | 6.0 ± 1.09 |
| 6 | | 0.0 ± 0.12 | 0.0 ± 0.27 | 1.34 ± 0.67 |
| 24 | | 0.0 ± 0.02 | 0.0 ± 0.03 | 0.0 ± 0.03 |

In summary, the present invention demonstrates that liposomal formulations of ciprofloxacin, vincristine and other alkaloids based on sphingomyelin/cholesterol vesicles have several significant advantages over formulations based on DSPC/cholesterol vesicles. Specifically, formulations based on sphingomyelin/cholesterol: (1) are much more stable to acid hydrolysis, (2) have significantly better drug retention characteristics, (3) have better tumor loading characteristics, and (4) show significantly better anti-tumor efficacy than do comparable liposomes composed of DSPC/Chol or SM/Chol/PEG-PE.

All publications and patents mentioned in this specification are herein incorporated by reference into the specification to the same extent as if each individual publication or patent was specifically and individually indicated to be incorporated herein by reference.

Although the foregoing invention has been described in some detail by way of illustration and example for purposes of clarity of understanding, it will be apparent that certain changes and modifications may be practiced within the scope of the appended claims.

What is claimed is:

1. A liposome for delivery of an alkaloid therapeutic compound, produced by the process of:

forming a liposome from a mixture which comprises sphingomyelin and cholesterol, in a first buffered aqueous solution having an acidic pH greater than pH 2; and suspending the liposome in a second buffered solution having a pH which is greater than that of the first buffered aqueous solution, whereby a transmembrane pH gradient is formed which facilitates the transfer of the therapeutic compound to the liposome.

2. The liposome produced by the process of claim 1, wherein the process further comprises the step of separating the liposome containing the therapeutic compound from the second buffer containing therapeutic compound which has not been entrapped by the liposome.

3. A liposome of claim 1, wherein the cholesterol is present in the liposomal composition at a total molar proportion of 30% to 50%.

4. A liposome of claim 1, wherein the sphingomyelin and cholesterol are present at a ratio of about 55/45, mol %/mol %, respectively.

5. A liposome of claim 1, wherein the alkaloid compound is vincristine or swainsonine.

6. A liposome of claim 1, wherein the alkaloid compound is vincristine.

7. A liposome of claim 1, wherein the alkaloid compound is swainsonine.

8. A liposome of claim 1, wherein the liposomes are unilamellar.

9. A liposome of claim 1, wherein the liposomes have mean diameters of about 0.05 microns to 0.45 microns.

10. A liposome of claim 1, wherein the liposomes have mean diameters of about 0.05 microns to 0.2 microns.

11. A liposome of claim 1, wherein the interior of said liposome is pH 2 to pH 5.

12. A liposome of claim 1, wherein the interior comprises a citrate buffer at about pH 4.0.

* * * * *